(12) United States Patent
Scheffler et al.

(10) Patent No.: US 9,844,522 B2
(45) Date of Patent: Dec. 19, 2017

(54) NICLOSAMIDE AND ITS DERIVATIVES FOR USE IN THE TREATMENT OF SOLID TUMORS

(71) Applicants: LIFE & BRAIN GMBH, Bonn (DE); RHEINISCHE FRIEDRICH-WILHELMS UNIVERSITÄT, Bonn (DE)

(72) Inventors: Björn Scheffler, Bonn (DE); Martin Glas, Bonn (DE); Anja Wieland, Watchtberg (DE)

(73) Assignees: LIFE & BRAIN GMBH, Bonn (DE); RHEINISCHE FRIEDRICH-WILHELMS UNIVERSITAT BONN, Bonn (DE)

( * ) Notice: Subject to any disclaimer, the term of this patent is extended or adjusted under 35 U.S.C. 154(b) by 0 days.

(21) Appl. No.: 14/420,164

(22) PCT Filed: Aug. 6, 2013

(86) PCT No.: PCT/EP2013/066484
§ 371 (c)(1),
(2) Date: Feb. 6, 2015

(87) PCT Pub. No.: WO2014/023732
PCT Pub. Date: Feb. 13, 2014

(65) Prior Publication Data
US 2015/0174086 A1  Jun. 25, 2015

(30) Foreign Application Priority Data

Aug. 6, 2012 (WO) .................. PCT/EP2012/065364

(51) Int. Cl.
| | |
|---|---|
| A61K 31/167 | (2006.01) |
| A61K 45/06 | (2006.01) |
| A61K 31/4188 | (2006.01) |
| A61K 31/609 | (2006.01) |
| G01N 33/574 | (2006.01) |
| C07C 235/64 | (2006.01) |
| C12Q 1/68 | (2006.01) |

(52) U.S. Cl.
CPC ........ *A61K 31/167* (2013.01); *A61K 31/4188* (2013.01); *A61K 31/609* (2013.01); *A61K 45/06* (2013.01); *C07C 235/64* (2013.01); *C12Q 1/6883* (2013.01); *G01N 33/57484* (2013.01); *C12Q 2600/156* (2013.01); *C12Q 2600/16* (2013.01); *G01N 2800/52* (2013.01)

(58) Field of Classification Search
CPC .................................................. C07D 400/12
See application file for complete search history.

(56) References Cited

U.S. PATENT DOCUMENTS

| | | |
|---|---|---|
| 2006/0009406 A1 | 1/2006 | Kyrkanides et al. |
| 2006/0009506 A1 | 1/2006 | Westwick et al. |

FOREIGN PATENT DOCUMENTS

| | | |
|---|---|---|
| EP | 1 454 898 | 9/2004 |
| WO | 02/46164 | 6/2002 |
| WO | 2003/053926 | 7/2003 |
| WO | 2004/006906 | 1/2004 |
| WO | 2005/060951 | 7/2005 |
| WO | 2006/097323 | 9/2006 |
| WO | 2006/122007 | 11/2006 |
| WO | 2009/148623 | 12/2009 |
| WO | 2010/078916 | 7/2010 |
| WO | 2012/172069 | 12/2012 |
| WO | 2013/019469 | 2/2013 |
| WO | 2013/049045 | 4/2013 |

OTHER PUBLICATIONS

McMahon et al. (2000).*
Pinedo et al. (2000).*
International Search Report dated Nov. 25, 2013 in International Application No. PCT/EP13/66484.
English translation of Japanese Office Action issued in connection with Japanese Application No. 2015-525864, dated May 16, 2017, 4 pages.
Partial English translation of abstract from "Multiple drug combination chemotherapy with temozolomide", Cancer and Chemotherapy, 2009, vol. 36, No. 6, p. 938-940.
Pan et al., "Niclosamide, an old antihelminthic agent, demonstrates antitumor activity by blocking multiple singalling pathways of cancer stem cells", vol. 31: 178-184.
Reh et al., "O6-methylguanine DNA adducts associated with occupational nitrosamine exposure", Carcinogenesis, 21: 29-33.
Walton et al., "Derivation and large-scale expansion of multipotent astroglial neural progenitors from adult human brain", Development 2006; 133(18): 3671-81.
Scheffler et al., "Phenotypic and functional characterization of adult brain neuropoiesis" Proc Natl Acad Sci USA 2005; 102(26):9353-8.
Chabner et al., "Timeline: Chemotherapy and the war on cancer", Nat. Rev. Cancer 5:65-72.
Hegi et al., "MGMT gene silencing and benefit from temozolomide in glioblastoma", N.Engl. J Med 352:997-1003.
Stupp et al. 2009. Effects of radiotherapy with concomitant and adjuvant temozolomide versus radiotherapy alone on survival in glioblastoma in a randomised phase III study: 5-year analysis of the EORTC-NCIC trial. Lancet Oncol. 10:459:466.
Swinney et al., "How were new medicines discovered?" Nat Rev Drug Discov 2011. 10:507-519.
Kola et al., 2004. "Can the pharmaceutical industry reduce attrition rates?", Nat Rev Drug Discov 3:711-715.
Paul V. Ward, "Contemporary pre-clinical development of anticancer agents-what are the optimal preclinical models?" Eur J Cancer 45 :2768-2781.
Sharma et al., 2010. Cell line-based platforms to evaluate the therapeutic efficacy of candidate anticancer agents. Nat Rev Cancer 10:241-253.

(Continued)

*Primary Examiner* — Paul V. Ward

(57) ABSTRACT

The present invention relates to novel therapeutic uses of niclosamide for the treatment of cancer. In particular, a combination of niclosamide or one of its derivatives with an alkylating agent is provided for the treatment of solid tumors. Moreover, niclosamide or one of its derivatives can be used for the treatment of solid tumors characterized by underexpression of NFKBIA. Finally, the invention relates to diagnostic methods for determining whether treatment with niclosamide alone or in combination with an alkylating agent is suitable for a cancer patient.

17 Claims, 21 Drawing Sheets

(56) References Cited

OTHER PUBLICATIONS

Figure 1:
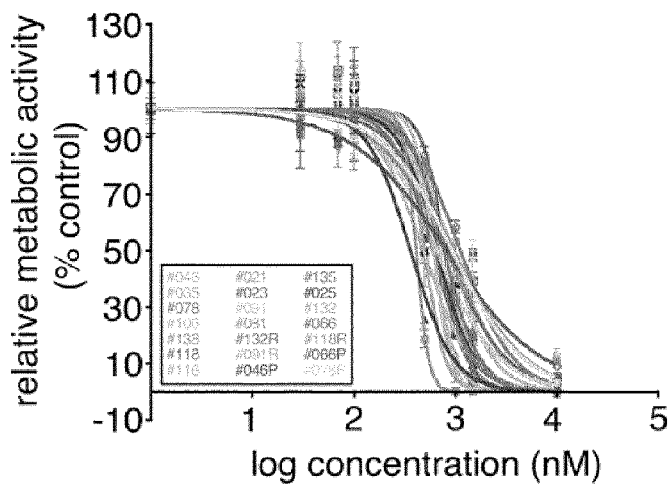
Figure 1:
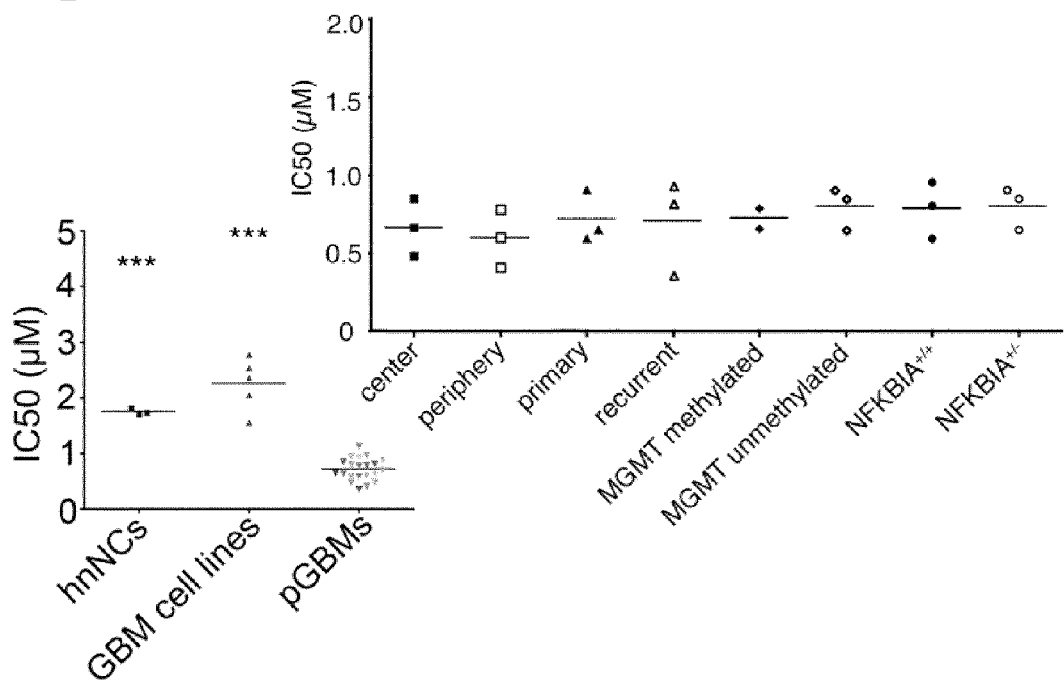

Lee et al. 2006. Tumor stem cells derived from glio blastomas cultured in bFGF and EGF more closely mirror the phenotype and genotype of primary tumors than do serum-cultured cell lines. Cancer Cell 9:391-403.
Pollard et al. 2009. Glioma stem cell lines expanded in adherent culture have tumor-specific phenotypes and are suitable for chemical and genetic screens. Cell Stem Cell 4:568-580.
Glas, et al. 2010. Residual tumor cells are unique cellular targets in glioblastoma. Ann Neurol 68:264-269.
Sack et al., 2011. Novel effect of antihelminthic Niclosamide on S100A4-mediated metastatic progression in colon cancer. J Natl Cancer Inst 103:1018-1036.
Osada, et al. 2011. Antihelminth compound niclosamide downregulates Wnt signaling and elicits antitumor responses in tumors with activating APC mutations. Cancer Res 71:4172-4182.
Simpson et al., 2006. Recurrent glioblastoma multiforme: advances in treatment and promising drug candidates. Expert Rev Anticancer Ther 6:1593-1607.
Weller, et al. 2010. MGMT promoter methylation in malignant gliomas: ready for personalized medicine? Nat Rev Neurol 6:39-51.
Bredel et al. 2011. NFKBIA deletion in glioblastomas. N Engl J Med 364:627-637.
Stiles et al., 2008. Glioma stem cells: a midterm exam. Neuron 58:832-846.
Zhou, et al., 2009. Tumour-initiating cells: challenges and opportunities for anticancer drug discovery. Nat Rev Drug Discov 8:806-823.
Nguyen et al., 2012. Cancer stem cells: an evolving concept. Nat Rev Cancer 12:133-143.
Westphal et al., 2011. The neurobiology of gliomas: from cell biology to the development of therapeutic approaches. Nat Rev Neurosci 12:495-508.
Darnell, J.E., Jr. 2002. Transcription factors as targets for cancer therapy. Nat Rev Cancer 2:740-749.
Balgi et al., 2009. Screen for chemical modulators of autophagy reveals novel therapeutic inhibitors of mTORCI signaling. PLoS One 4:e7124.
Wang et al., 2009. The autonomous notch signal pathway is activated by baicalin and baicalein but is suppressed by niclosamide in K562 cells. J Cell Biochem 106:682-692.
Jin, 2010. Antineoplastic mechanisms of niclosamide in acute myelogenous leukemia stem cells: inactivation of the NF-kappaB pathway and generation of reactive oxygen species. Cancer Res 70:2516.
Wullschleger, 2006. TOR signaling in growth and metabolism. Cell 124:471-484.
Fang et al. 2007. Phosphorylation of beta-catenin by AKT promotes beta-catenin transcriptional activity. J Biol Chem 282:11221-11229.
Clevers, H. 2006. Wnt/beta-catenin signaling in development and disease. Cell 127:469-480.
Moon et al., 2004. WNT and beta-catenin signalling: diseases and therapies. Nat Rev Genet 5:691-701.
Bredel et al., 2006. Tumor necrosis factor-alpha-induced protein 3 as a putative regulator of nuclear factor-kappaB-mediated resistance to alkylating agents in human glioblastomas. J Clin Oncol 24:274-287.
Baldwin, A.S. 2001. Control of oncogenesis and cancer therapy resistance by the transcription factor NF-kappaB. J Clin Invest 107:241-246.
Nakanishi et al., 2005. Nuclear factor-kappaB inhibitors as sensitizers to anticancer drugs. Nat Rev Cancer 5:297-309.
Brada et al., 1999. Phase I dose-escalation and pharmacokinetic study of temozolomide (SCH 52365) for refractory or relapsing malignancies. Br J Cancer 81: 1022-1030.
Hermisson, 2006. 06-methylguanine DNA methyltransferase and p53 status predict temozolomide sensitivity in human malignant glioma cells. J N eurochem 96: 7 66-776.
Beier et al. 2008. Temozolomide preferentially depletes cancer stem cells in glioblastoma. Cancer Res 68:5706-5715.
Chou, 2010. Drug combination studies and their synergy quantification using the Chou-Talalay method. Cancer Res 70:440-446.
Bonavia, 2011. Heterogeneity maintenance in glioblastoma: a social network. Cancer Res 71:4055-4060.
Andrews et al., 1982. The biology and toxicology of molluscicides, Bayluscide. Pharmacol Ther 19:245-295.
Zhang et al. 2011. FoxMI promotes beta-catenin nuclear localization and controls Wnt target-gene expression and glioma tumorigenesis. Cancer Cell 20:427-442.
Zhu et al. 2011. Endothelial cells create a stem cell niche in glioblastoma by providing NOTCH ligands that nurture self-renewal of cancer stem-like cells. Cancer Res 71:6061-6072.
Akhavan, D., Cloughesy, T.F., and Mischel, P.S. 2010. mTOR signaling in glioblastoma: lessons learned from bench to bedside. Neuro Oncol 12:882-889.
Barretina et al. 2012. The Cancer Cell Line Encyclopedia enables predictive modelling of anticancer drug sensitivity. Nature 483:603-607.
Cao et al. 1995. Defective lymphoid development in mice lacking expression of the common cytokine receptor gamma chain. Immunity 2:223-238.
Louis et al., 2007. The 2007 WHO classification of tumours of the central nervous system. Acta Neuropathol 114:97-109.
Mikeska et al. 2007. Optimization of quantitative MGMT promoter methylation analysis using pyrosequencing and combined bisulfite restriction analysis. J Mol. Diagn. 9:368-381.
Koch et al., 2009. A rosette-type, self-renewing human ES cell-derived neural stem cell with potential for in vitro instruction and synaptic integration. Proc Natl Acad Sci US A 106:3225-3230.
Falk et al. 2012. Capture of neuroepithelial-like stem cells from pluripotent stem cells provides a versatile system for in vitro production of human neurons. PLoS One 7:e29597.
Koch et al., 2011. Excitation-induced ataxin-3 aggregation in neurons from. patients with Machado-Joseph disease. Nature.
Goetz et al., 2006. Temporally restricted substrate interactions direct fate and specification of neural precursors derived from. embryonic stem. cells. Proc Natl Acad Sci US A 103:11063-11068.
Wiechen et al. 2001. Caveolin-1 is down• regulated in hum.an ovarian carcinoma and acts as a candidate tum.or suppressor gene. Am. J Pathol 159:1635-1643.
Ishikawa et al., "Medication Strategy for Malignant Glioma", Jpn. J. Pharm. Health Care Sci., vol. 32, pp. 1081-1087, 2006 (English Abstract Provided).
Kitasato, "Glioblastoma: temozolomide", Medicine, vol. 39, 2009 (No English Translation Available).

\* cited by examiner

A

B

C

A

B

C

D

E

F

A

B

A

B

| pGBM # | NFKBIA status | Expected survival propotion | Observed survival proportion | Combinatorial index |
|---|---|---|---|---|
| 046 | +/- | 0.667 | 0.444 | 0.665 |
| 078 | +/- | 0.574 | 0.426 | 0.742 |
| 118 | +/- | 0.831 | 0.496 | 0.596 |
| 138 | +/- | 0.551 | 0.396 | 0.718 |
| 066 | +/+ | 0.705 | 0.720 | 0.979 |
| 081 | +/+ | 0.496 | 0.447 | 0.901 |
| 106 | +/+ | 0.785 | 0.752 | 0.957 |

C

Fig. 17

| pGBM | NFKBIA | screening | Pharma | CT/LT | FACS | NSA | kinetics | WB | qPCR | transplantation | SNP |
|---|---|---|---|---|---|---|---|---|---|---|---|
| 021 | +/+ | - | 8 | - | - | - | - | - | - | - | 6 |
| 023 | +/+ | 10 | 9 | - | - | - | - | - | - | - | 7 |
| 025 | +/+ | - | 8 | - | - | - | - | - | - | - | 7 |
| 035 | +/+ | 10 | 8-12 | 10 | 9-11 | - | 8 | 10/11 | 9/10 | - | 5 |
| 046 | +/- | 10 | 8-12 | 10 | 9-11 | 9 | 8 | 10/11 | 9/10 | 12 | 5 |
| 066 | +/+ | - | 8-12 | - | - | - | 8 | 10/11 | 9/10 | - | 5 |
| 078 | +/- | - | 8-12 | 10 | 9-11 | 9 | - | 10/11 | 9/10 | - | 5 |
| 081 | +/+ | - | 9-12 | - | 11 | - | - | 10/11 | 9/10 | - | 5 |
| 91 | n.d. | - | 11 | - | - | - | - | - | - | - | - |
| 106 | +/+ | 10 | 8-12 | 10 | 9-11 | 9 | 8 | 10/11 | 9/10 | - | 6 |
| 116 | n.d. | - | 11 | - | - | - | - | - | - | - | - |
| 118 | +/- | - | 9-12 | - | - | - | - | 10/11 | 9/10 | - | 7/6 |
| 132 | n.d. | - | 10 | - | - | - | - | - | - | - | - |
| 135 | +/- | - | 8 | - | - | - | - | - | - | - | 7 |
| 138 | +/- | - | 9-12 | - | - | - | - | 10/11 | 9/10 | - | 5 |
| GNV019 | +/++ | - | 11 | - | - | 11 | - | - | - | 11 | 3/10 |

NICLOSAMIDE AND ITS DERIVATIVES FOR USE IN THE TREATMENT OF SOLID TUMORS

CROSS-REFERENCE TO RELATED APPLICATIONS

This application is a US National Phase filing of PCT/EP2013/066484, filed on Aug. 6, 2013, which claims priority of PCT/EP2012/065364, filed on Aug. 6, 2012, the entire disclosures of which are hereby expressly incorporated by reference.

The present invention relates to novel therapeutic uses of niclosamide for the treatment of cancer. In particular, a combination of niclosamide or one of its derivatives with an alkylating agent is provided for the treatment of solid tumors. Moreover, niclosamide or one of its derivatives can be used for the treatment of solid tumors characterized by underexpression of NFKBIA. Finally, the invention relates to diagnostic methods for determining whether treatment with niclosamide alone or in combination with an alkylating agent is suitable for a cancer patient.

BACKGROUND OF THE INVENTION

Chemotherapy has developed to an increasingly effective line of defense against cancer (1). In glioblastoma (GBM), the alkylating agent temozolomide (TMZ) has become a standard, in combination with surgical resection and radiotherapy. There is nevertheless a considerable need to develop alternative treatment options, as GBM remains a fatal disease with a median overall survival of only 15 months (2, 3). For anticancer drug discovery, two major strategies are traditionally employed (4). One is the targeted approach where cancer-related molecules and/or signaling cascades need to be exposed before specific compounds can be designed for distinct interference and inhibition. Alternatively, empirical screening of hundreds to thousands of compounds can be conducted to identify otherwise unpredictable antineoplastic effects. Both strategies, however, are burdened with high attrition rates during clinical translation (5, 6). This may in part be caused by the use of inept cellular model systems for drug evaluation at early developmental stages (7), e.g. inter- and intra-patient tumor heterogeneity is rarely reflected within these systems. The present inventors have developed an in vitro cellular system that is closely mirroring GBM in vivo and is, thus, particular suitable to identify compounds and combinations of compounds that are likely to also provide GBM specific anticancer activity when used in vivo. Using this in vitro cellular system the present inventors were able to identify compounds and compound combinations for the improved chemotherapy of glioblastoma.

SUMMARY OF THE INVENTION

In a first aspect the invention relates to a combination of a first cytostatic compound according to formula I, II or III

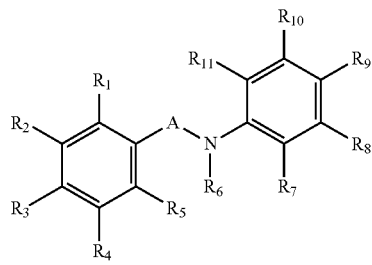

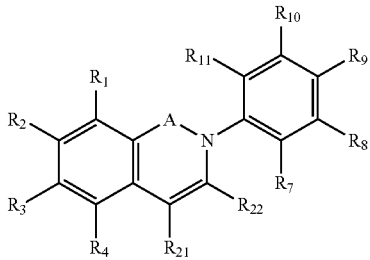

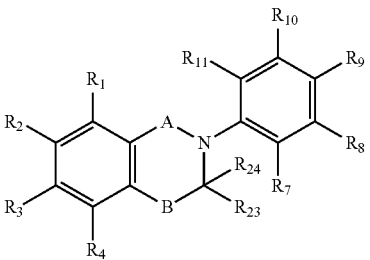

wherein

A is carbonyl, methylene, hydroxymethinyl, alkoxymethinyl, aminomethinyl, oxime, hydrazone, arylhydrazone, or semicarbazone;

B if present is $CR_{25}R_{26}$, O, S or $NR_{27}$;

$R_1$, $R_3$, $R_4$, $R_8$, $R_{10}$, and $R_{11}$ are independently hydrogen; hydroxyl, alkoxy; halogen; or $C_1$ to $C_6$ alkyl;

$R_2$ and $R_7$ are independently halogen, hydroxyl or hydrogen, $R_5$ if present is hydroxyl, phosphate, hydrogen, halogen, alkyl, cycloalykyl, alkenyl, alkynyl, aryl, alkoxy, alkylthio or amino;

$R_6$ if present is hydrogen or $C_1$ to $C_6$ alkyl;

$R_9$ is nitro, hydrogen, hydroxyl, amino, halogen, alkyl, alkenyl, alkynyl, or aryl; and $R_{21}$, $R_{22}$, $R_{23}$, and $R_{24}$, if present are independently hydrogen, hydroxyl, halogen, alkyl, alkenyl, alkynyl, cycloalkyl or aryl;

$R_{25}$ and $R_{26}$ if present are independently hydrogen, hydroxyl, halogen, alkyl, alkenyl, alkynyl, cycloalkyl or aryl; and $R_{27}$ if present is hydrogen or $C_1$ to $C_6$ alkyl;

or salt thereof;

and an alkylating compound for use in treating of a solid tumor.

In an aspect of the invention, the alkylating compound has a structure according to formula IV

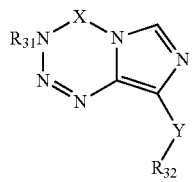

(IV)

wherein

X and Y are independently carbonyl, methylene, hydroxymethinyl, alkoxymethinyl, aminomethinyl, oxime, hydrazone, arylhydrazone or semicarbazone, $R_{31}$ is hydrogen, alkyl, alkoxy, alkenyl, alkynyl, cycloalkyl or aryl; and $R_{32}$ is amino, hydrogen, hydroxyl or halogen or salt thereof.

In a further aspect, the present invention relates to a pharmaceutical composition comprising a compound according to formula I, II or III, wherein A, B, $R_1$ to $R_{11}$ and $R_{21}$ to $R_{24}$ have a meaning as defined above, an alkylating agent and a pharmaceutically acceptable excipient for use in treating of a solid tumor.

In yet a further aspect, the present invention relates to a compound according to formula I, II or III, wherein A, B, $R_1$ to $R_{11}$ and $R_{21}$ to $R_{24}$ have a meaning as defined above for use in treating a solid tumor characterized by a decreased expression level NFKBIA.

In yet a further aspect, the present invention relates to a method for determining if therapy with the cytostatic compound according to formula I, II or III as defined supra is suitable for treating a patient with a solid tumor comprising the steps of a) determining the expression level of NFKBIA in a sample of tumor cells or tumor tissue of the patient;

b) comparing the determined expression level with a reference value;

c) determining if the therapy with niclosamide is suitable for the patient based on the result of the comparison of step b), wherein underexpression or a deletion of NFKBIA indicates that the combination therapy is suitable for the patient.

In yet another aspect, the present invention relates to a method for determining the molar ratio of niclosamide to temozolomide to be administered to a patient with a solid tumor comprising the steps of a) determining the expression level of NFKBIA in a sample of tumor cells or tumor tissue of the patient;

b) comparing the determined expression level with a reference value;

c) determining the molar ratio of niclosamide to temozolomide based on the result of the comparison of step b), wherein (i) an expression above the reference value indicates that the molar ratio shall be below 40% niclosamide; and (ii) an expression level below the reference value indicates that the molar ratio shall be larger than or equal to 40% niclosamide.

DETAILED DESCRIPTION OF THE INVENTION

Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In order to identify novel compounds suitable for the treatment of solid tumors, in particular glioblastoma, primary human GBM cells known to retain patient- and disease-specific traits in vitro (pGBMs) (8-10), were applied in an empirical screening approach. Drug discovery and validation was conducted on a portfolio of pGBMs representing multiple facets of the disease. Three independent human non-malignant neural cell populations (hnNCs) as well as five commonly used glioma cell lines served as control for the experiments. The small molecule niclosamide emerged from these studies as pGBM-selective, pro-apoptotic, and antiproliferative compound. Niclosamide's pleiotropic mode of action effectively depleted GBM cells with and without stem cell qualities, and it significantly increased survival times in xenograft models. A synergistic anticancer activity in combination with TMZ and an associated biomarker for these effects furthermore suggested unique perspectives for the clinical development of niclosamide as an addition to current standards in the primary therapy of GBM.

Thus, the problem underlying the present invention is solved by the provision of a combination of a first cytostatic compound according to formula I, II or III

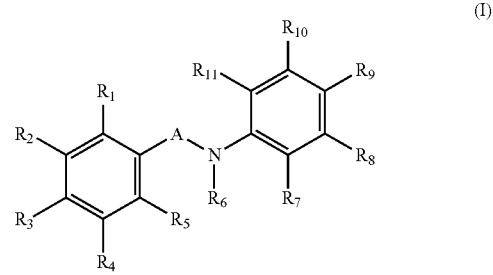

(I)

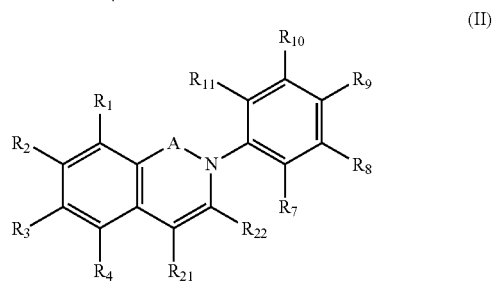

(II)

-continued

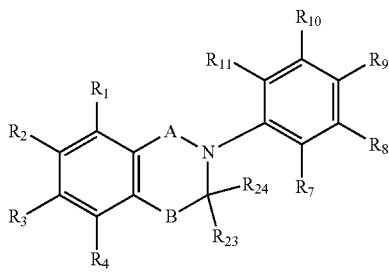

(III)

wherein
A is carbonyl, methylene, hydroxymethinyl, alkoxymethinyl, aminomethinyl, oxime, hydrazone, arylhydrazone, or semicarbazone, preferably carbonyl;

B if present is $CR_{25}R_{26}$, O, S or $NR_{27}$;

$R_1$, $R_3$, $R_4$, $R_8$, $R_{10}$, and $R_{11}$ are independently hydrogen; hydroxyl; alkoxy, preferably $C_1$ to $C_6$ alkoxy; halogen, preferably fluorine, chlorine, or bromine; or $C_1$ to $C_6$ alkyl, i.e. $C_1$, $C_2$, $C_3$, $C_4$, $C_5$, or $C_6$-alkyl, preferably in each case hydrogen;

$R_2$ and $R_7$ are independently halogen, hydroxyl or hydrogen, preferably in each case halogen;

$R_5$ is hydroxyl, phosphate, hydrogen; halogen, preferably fluorine, chlorine, or bromine; alkyl, preferably $C_1$ to $C_6$ alkyl, i.e. $C_1$, $C_2$, $C_3$, $C_4$, $C_5$, or $C_6$-alkyl; alkenyl, preferably $C_2$ to $C_6$ alkenyl; alkynyl, preferably $C_2$ to $C_6$ alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl; alkoxy, preferably $C_1$ to $C_6$ alkoxy; alkylthio, preferably $C_1$ to $C_6$ alkthio or amino; most preferably hydroxyl or phosphate;

$R_6$ if present is hydrogen or $C_1$ to $C_6$ alkyl;

$R_9$ is nitro, hydrogen, hydroxyl, amino; halogen, preferably fluorine, chlorine, or bromine; alkyl, preferably $C_1$ to $C_6$ alkyl, i.e. $C_1$, $C_2$, $C_3$, $C_4$, $C_5$, or $C_6$-alkyl; alkenyl, preferably $C_2$ to $C_6$ alkenyl; alkynyl, preferably $C_2$ to $C_6$ alkynyl; or aryl, preferably $C_6$ to $C_{14}$ aryl, preferably phenyl; most preferably nitro; and $R_{21}$, $R_{22}$, $R_{23}$, and $R_{24}$, if present, are independently hydrogen; hydroxyl; halogen, preferably fluorine, chlorine, or bromine; alkyl, preferably $C_1$ to $C_6$ alkyl, i.e. $C_1$, $C_2$, $C_3$, $C_4$, $C_5$, or $C_6$-alkyl; alkenyl, preferably $C_2$ to $C_6$ alkenyl; alkynyl, preferably $C_2$ to $C_6$ alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl;

$R_{25}$ and $R_{26}$ if present are independently hydrogen, hydroxyl, halogen, preferably fluorine, chlorine, or bromine; alkyl, preferably $C_1$ to $C_6$ alkyl, i.e. $C_1$, $C_2$, $C_3$, $C_4$, $C_5$, or $C_6$-alkyl; alkenyl, preferably $C_2$ to $C_6$ alkenyl; alkynyl, preferably $C_2$ to $C_6$ alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl; and $R_{27}$ if present is hydrogen or $C_1$ to $C_6$ alkyl;

or salt thereof;

and an alkylating compound for use in treating of a solid tumor.

A compound is a "cytostatic compound" as referred to in the present application, if it is capable of inhibiting the proliferation of tumor cells. Preferably, a cytostatic compound is also cytotoxic, i.e. it actually kills the tumor cells. Preferably, the aforementioned effects of a given concentration of a cytostatic compound affect tumor cells stronger than non-tumor cells so that healthy tissue is not damaged or less damaged by said compounds as compared to tumor tissue. A preferred method for determining the strength of the cytotoxic effect of a compound is the determination of the concentration which decreases the metabolic activity of a cell population to 50% of the activity of a control ($ICM_{50}$). This can, e.g., be done by applying resazurin to the cell culture. In healthy cells resazurin is converted to the fluorescent product resorufin. The rate of conversion can be used to measure the metabolic activity of a cell. Preferably, the cytostatic compound according to the present invention has an $ICM_{50}$ concentration which is not larger than 2-fold, 5-fold, 10-fold, 20-fold or 50-fold than the $ICM_{50}$ concentration of niclosamide or niclosamide and an alkylating agent in the same setting.

In a preferred embodiment of the present invention, the compound is defined by formula I, wherein A is carbonyl;

$R_1$, $R_3$, $R_4$, $R_8$, $R_{10}$, and $R_{11}$ are independently hydrogen, hydroxyl, halogen or $C_1$ to $C_6$ alkyl, preferably in each case hydrogen;

$R_2$ and $R_7$ are independently halogen, hydroxyl or hydrogen, preferably in each case halogen, more preferably fluorine, chlorine or bromine, most preferably chlorine;

$R_5$ is hydroxyl, phosphate; hydrogen; halogen, preferably fluorine, chlorine, or bromine; alkyl, preferably $C_1$ to $C_6$ alkyl, i.e. $C_1$, $C_2$, $C_3$, $C_4$, $C_5$, or $C_6$-alkyl; alkenyl, preferably $C_2$ to $C_6$ alkenyl, i.e. $C_2$, $C_3$, $C_4$, $C_5$, or $C_6$-alkenyl; alkynyl, preferably $C_2$ to $C_6$ alkynyl, i.e. $C_2$, $C_3$, $C_4$, $C_5$, or $C_6$-alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl; alkoxy, preferably $C_1$ to $C_6$ alkoxy; alkylthio, preferably $C_1$ to $C_6$ alkthio or amino; most preferably hydroxyl or phosphate; and $R_9$ is nitro, hydrogen, hydroxyl, amino, halogen, alkyl, alkenyl, alkynyl, or aryl, preferably nitro.

In a preferred embodiment of the present invention, the compound is defined by formula I, wherein A is carbonyl;

$R_1$, $R_3$, $R_4$, $R_8$, $R_{10}$, and $R_{11}$ are independently hydrogen; hydroxyl; halogen, preferably fluorine, chlorine, or bromine; or $C_1$ to $C_6$ alkyl, i.e. $C_1$, $C_2$, $C_3$, $C_4$, $C_5$, or $C_6$-alkyl; preferably in each case hydrogen;

$R_2$ and $R_7$ are independently halogen, preferably fluorine, chlorine, or bromine; hydroxyl or hydrogen; most preferably chlorine;

$R_5$ is hydroxyl, phosphate, hydrogen, halogen, preferably fluorine, chlorine, or bromine; alkyl, preferably $C_1$ to $C_6$ alkyl, i.e. $C_1$, $C_2$, $C_3$, $C_4$, $C_5$, or $C_6$-alkyl; alkenyl, preferably $C_2$ to $C_6$ alkenyl, i.e. $C_2$, $C_3$, $C_4$, $C_5$, or $C_6$-alkenyl; alkynyl, preferably $C_2$ to $C_6$ alkynyl, i.e. $C_2$, $C_3$, $C_4$, $C_5$, or $C_6$-alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl; alkoxy, preferably $C_1$ to $C_6$ alkoxy, i.e. $C_1$, $C_2$, $C_3$, $C_4$, $C_5$, or $C_6$-alkoxy; alkylthio, preferably $C_1$ to $C_6$ alkthio, i.e. i.e. $C_1$, $C_2$, $C_3$, $C_4$, $C_5$, or $C_6$-alkylthio; or amino; most preferably hydroxyl or phosphate; and $R_9$ is nitro.

Even more preferably in the compound defined by formula I

A is carbonyl;

$R_1$, $R_3$, $R_4$, $R_6$, $R_8$, $R_{10}$ and $R_{11}$ are hydrogen;

$R_2$ and $R_7$ are chlorine, $R_5$ is hydroxyl; and $R_9$ is nitro.

In another preferred embodiment of the present invention, the compound is defined by formula I, wherein A is carbonyl;

$R_1$, $R_3$, $R_4$, $R_6$, $R_8$, $R_{19}$ and $R_{11}$ are hydrogen;

$R_2$ and $R_7$ are chlorine, $R_5$ is phosphate; and $R_9$ is nitro.

In the most preferred embodiment the cytostatic compound is niclosamide.

It has been shown that a phosphate group significantly increases the resorption of the compound of formula I (Pan et al., 2012, Niclosamide, an old antihelminthic agent, demonstrates antitumor activity by blocking multiple signalling pathways of cancer stem cells, Vol. 31: 178-184), thus improving the bioavailability of this compound.

The term "alkylating agent" relates to any pharmaceutical compound which is capable of transforming guanine to $O^6$-alkylguanine, $O^4$-alkyguanine or $N^7$-alkylguanine, i.e. a $O^6$-alkylating agent, $O^4$-alkylating agent or a $N^7$-alkylating agent. Suitable alkylating agents are known to the skilled person. Typically, the alkyl group added by the alkylating agent is methyl. This transformation damages the DNA and triggers the death of the cell in question. This effect affects primarily rapidly dividing cells such as cancer cells. Alkylated guanine can be detected as described by Reh et al. (1999) "$O^6$-methylguanine DNA adducts associated with occupational nitrosamine exposure", Carcinogenesis, 21: 29-33. Preferably, the alkylating agent is an $O^6$-alkylating agent, i.e. it exclusively or primarily alkylates the $C^6$-atom of guanine.

In an aspect of the invention, the alkylating compound has a structure according to formula IV

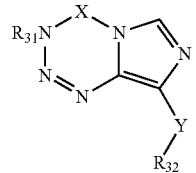

(IV)

wherein

X and Y are independently carbonyl, methylene, hydroxymethinyl, alkoxymethinyl, aminomethinyl, oxime, hydrazone, arylhydrazone or semicarbazone, preferably carbonyl, $R_{31}$ is alkyl, preferably $C_1$ to $C_6$ alkyl, i.e. $C_1$, $C_2$, $C_3$, $C_4$, $C_5$, or $C_6$-alkyl; hydrogen; alkoxy, preferably $C_1$ to $C_6$ alkoxy, i.e. $C_1$, $C_2$, $C_3$, $C_4$, $C_5$, or $C_6$-alkoxy, alkenyl, preferably $C_2$ to $C_6$ alkenyl, i.e. $C_2$, $C_3$, $C_4$, $C_5$, or $C_6$-alkenyl; alkynyl, preferably $C_2$ to $C_6$ alkynyl, i.e. $C_2$, $C_3$, $C_4$, $C_5$, or $C_6$-alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl; preferably alkyl; and $R_{32}$ is amino, hydrogen, hydroxyl or halogen, preferably fluorine, chlorine, or bromine;

or salt thereof.

In a preferred embodiment the alkylating agent is defined by formula IV X is carbonyl and Y is carbonyl, methylene, hydroxymethinyl, alkoxymethinyl, aminomethinyl, oxime, hydrazone, arylhydrazone or semicarbazone, preferably carbonyl, $R_{31}$ is alkyl, preferably $C_1$ to $C_6$ alkyl, i.e. $C_1$, $C_2$, $C_3$, $C_4$, $C_5$, or $C_6$-alkyl; hydrogen; alkoxy, preferably $C_1$ to $C_6$ alkoxy, i.e. $C_1$, $C_2$, $C_3$, $C_4$, $C_5$, or $C_6$-alkoxy, alkenyl, preferably $C_2$ to $C_6$ alkenyl, i.e. $C_2$, $C_3$, $C_4$, $C_5$, or $C_6$-alkenyl; alkynyl, preferably $C_2$ to $C_6$ alkynyl, i.e. $C_2$, $C_3$, $C_4$, $C_5$, or $C_6$-alkynyl; cycloalkyl, preferably $C_3$ to $C_8$ cycloalkyl, in particular cyclopentyl, cyclohexyl, cycloheptyl and cyclooctyl; or aryl, preferably $C_6$ to $C_{14}$ aryl, in particular phenyl; preferably alkyl; and $R_{32}$ is amino, hydrogen, hydroxyl or halogen, preferably fluorine, chlorine, or bromine;

or salt thereof.

In an especially preferred embodiment the alkylating agent is defined by formula IV, wherein X and Y are carbonyl;

$R_{31}$ is alkyl, preferably $C_1$ to $C_6$ alkyl, i.e. $C_1$, $C_2$, $C_3$, $C_4$, $C_5$, or $C_6$-alkyl, preferably methyl; and $R_{32}$ is amino.

In the most preferred embodiment the alkylating agent is temozolomide.

The terms used above have the following preferred meanings:

Alkyl groups are, preferably, straight-chained or branched $C_1$ to $C_{10}$ alkyl groups, more preferably $C_1$ to $C_6$ alkyl groups. Alkyl groups comprising not more than 6 carbon atoms are referred to as "lower alkyl". Preferred alkyl groups comprise methyl, ethyl, propyl, isopropyl, butyl, sec-butyl, tert-butyl, 3-pentyl, hexyl and octyl groups.

Preferred cycloalkyl groups are $C_3$ to $C_8$ cycloalkyl, in particular cyclopentyl, cyclohexyl, cycloheptyl and cyclooctyl. Further preferred are the corresponding cycloalkenyl groups, in particular cyclopentenyl, cyclohexenyl, cycloheptenyl and cyclooctenyl.

Preferred alkenyl groups are $C_2$ to $C_{10}$ alkenyl, in particular ethenyl, 1- or 2-propenyl, 1-, 2- or 3-butenyl, 1-, 2-, 3- or 4-pentenyl, 1-, 2-, 3-, 4- or 5-hexenyl, 1-, 2-, 3-, 4-, 5- or 6-heptenyl, 1-, 2-, 3-, 4-, 5-, 6- or 7-oktenyl, 1-, 2-, 3-, 4-, 5-, 6-, 7- or 8-nonenyl or 1-, 2-, 3-, 4-, 5-, 6-, 7-, 8- or 9-decenyl.

Preferred alkynyl groups are $C_2$ to $C_{10}$ alkynyl, in particular ethenyl, 1- or 2-propynyl, 1-, 2- or 3-butynyl, 1-, 2-, 3- or 4-pentynyl, 1-, 2-, 3-, 4- or 5-hexynyl, 1-, 2-, 3-, 4-, 5- or 6-heptynyl, 1-, 2-, 3-, 4-, 5-, 6- or 7-oktynyl, 1-, 2-, 3-, 4-, 5-, 6-, 7- or 8-nonynyl or 1-, 2-, 3-, 4-, 5-, 6-, 7-, 8- or 9-decynyl.

The terms "alkyl group", "cycloalkyl group", "alkenyl group" and "alkynyl group" also refer to substituted alkyl, cycloalkyl, alkenyl and alkynyl groups. Preferred substituents of the said groups comprise at least one halogen, hydroxyl, carboxyl, alkoxycarbonyl, amino, nitro, cyano, $C_1$ to $C_6$ acylamino, $C_1$ to $C_6$ aminoacyl, $C_1$ to $C_6$ acyloxy, $C_1$ to $C_6$ alkoxy, aryloxy, alkylthio, $C_6$ to $C_{10}$ aryl, $C_4$ to $C_7$ cycloalkyl, $C_2$ to $C_6$ alkenyl and $C_2$ to $C_6$ alkynyl.

Preferred alkoxy groups comprise oxygen substituted by one of the alkyl, alkenyl or alkynyl groups recited above, preferably by methyl, ethyl, propyl, isopropyl, butyl, sec-butyl, tert-butyl, 3-pentyl, hexyl and octyl groups, more preferably methyl.

Preferred alkylthio groups comprise sulphur substituted by one of the alkyl, alkenyl or alkynyl groups recited above, preferably by methyl, ethyl, propyl, isopropyl, butyl, sec-butyl, tert-butyl, 3-pentyl, hexyl and octyl groups, more preferably methyl, sulfoxides and sulfones.

Preferred amino groups comprise —$NH_2$, —$NHR_{51}$, —$NR_{51}R_{52}$, wherein $R_{51}$ and $R_{51}$ are $C_1$ to $C_{10}$ alkyl, preferably selected from the groups methyl, ethyl, propyl, isopropyl, butyl, sec-butyl, tert-butyl, 3-pentyl, hexyl and octyl groups, most preferably methyl, or cycloalkyl groups or $R_{51}$ and $R_{52}$ are combined with the N to form a ring structure, preferably a 5 to 7 membered ring structure, such as piperidine or $R_{51}$ and $R_{52}$ are combined with the N and another heteroatom to form a saturated, substituted, or partially saturated 5-7-membered heterocyclo group. Preferred heteroatoms include O, N and S.

Preferred aryl groups comprise $C_6$ to $C_{14}$ aryl, more particularly $C_6$ to $C_{10}$ aryl. More preferably, the aryl group is phenyl, naphtyl, phenanthrenyl, anthracenyl, indenyl, azulenyl, bephenyl, biphenylenyl or fluorenyl. The term "aryl group" also refers to substituted aryl groups as defined below.

Preferred substituents of the aryl, groups comprise at least one acyl, alkylenedioxy (—$OCH_2O$—), halogen, $C_6$ to $C_{10}$ aryl, $C_4$ to $C_7$ cycloalkyl, $C_1$ to $C_6$ alkyl, $C_2$ to $C_6$ alkenyl, $C_2$ to $C_6$ alkynyl, $C_1$ to $C_6$ hydroxyalkyl, nitro, amino or $C_1$ to $C_6$ alkoxy group.

Preferred halogens comprise fluorine, iodine, chlorine and bromine.

In another preferred embodiment, the alkylating agent is selected from the group consisting of nitrogen mustards, nitrosoureas, alkyl sulfonates, platinum-based chemotherapeutic drugs and non-classical alkylating agents.

Preferred nitrogen mustards are cyclophosphamide, mechlorethamine, uramustine, melphalan, chlorambucil, trofosfamide and ifosfamide.

Preferred nitrosoureas are carmustine, lomustine and streptozocin.

A preferred alkyl sulfonate is busulfan.

Preferred platinum-based chemotherapeutic drugs are cisplatin, carboplatin, nedaplatin, oxaliplatin, satraplatin and triplatin tetranitrate.

Preferred non-classical alkylating agents are procarbazine, altetramine, dacarbazine, thiotepa and mitozolomide. Particularly preferred are dacarbazine and mitozolomide.

Most preferably, the alkylating agent is a nitrosourea, in particular carmustine.

The term "solid tumor" refers to any coherent group of neoplastic cells. A "solid tumor" according to the present application may be benign, pre-malign or malign. Preferably, it is pre-malign or malign and, most preferably, malign.

Preferred pre-malign tumors are selected from the group consisting of actinic keratosis, cutaneaous horn, actinic cheilitis, tar keratosis, arsenic keratosis, x-ray keratosis, Bowen's disease, bowenoid papulosis, lentigo maligna, lichen sclerosus, and lichen rubber mucosae; precancerosis of the digestive tract, in particular erythroplakia, leukoplakia, Barrett's esophagus, Plummer-Vinson syndrome, crural ulcer, gastropathia hypertrophica *gigantea*, borderline carcinoma, neoplastic intestinal polyp, rectal polyp, porcelain gallbladder; gynaecological precancerosis, in particular carcinoma ductale in situ (CDIS), cervical intraepithelial neoplasia (CIN), leukoplakia, endometrial hyperplasia (grade III), vulvar dystrophy, vulvar intraepithelial neoplasia (VIN), hydatidiform mole; urologic precancerosis, in particular bladder papillomatosis, Queyrat's erythroplasia, testicular intraepithelial neoplasia (TIN), leukoplakia and carcinoma in situ (CIS).

Preferred malign tumors are selected from the group consisting of glioblastoma, diffuse large B-cell lymphoma (DLBCL), T-cell lymphomas, e.g., cutaneous T-cell lymphoma (CTCL), noncutaneous peripheral T-cell lymphoma, lymphoma associated with human T-cell lymphotrophic virus (HTLV), adult T-cell lymphoma (ATLL), Hodgkin's lymphoma, non-Hodgkin's lymphoma (including primary central nervous system lymphoma), multiple myeloma, multiple myeloma, mesothelioma, childhood solid tumors, bone cancer and soft-tissue sarcomas, common solid tumors of adults such as head and neck cancers (e.g., oral, laryngeal and esophageal), genitourinary cancers (e.g., prostate, bladder, renal (in particular malignant renal cell carcinoma (RCC)), uterine, ovarian, testicular), colorectal carcinoma, lung cancer (e.g., small cell carcinoma and non-small cell lung carcinoma, including squamous cell carcinoma and adenocarcinoma), breast cancer, pancreatic cancer, melanoma and other skin cancers, basal cell carcinoma, metastatic skin carcinoma, squamous cell carcinoma of both ulcerating and papillary type, stomach cancer, brain cancer, hepatocellular carcinoma, adrenal cancer, kidney cancer, thyroid cancer, medullary carcinoma, osteosarcoma, soft-tissue sarcoma, Ewing's sarcoma, veticulum cell sarcoma, and Kaposi's sarcoma, fibrosarcoma, myxo sarcoma, liposarcoma, chondrosarcoma, osteogenic sarcoma, chordoma, angiosarcoma, endotheliosarcoma, lymphangiosarcoma, lymphangio endothelio sarcoma, synovioma, mesothelioma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, astrocytoma, medulloblastoma, craniopharyngioma, ependymoma, pinealoma, hemangioblastoma, acoustic neuroma, oligodendroglioma, meningioma, neuroblastoma, retinoblastoma, hemangioma, heavy chain disease and metastases.

In a preferred embodiment of the present invention, the solid tumor is selected from the group consisting of glioblastoma, Hodkin's lymphoma, colorectal cancer, melanoma hepatocellular carcinoma, breast cancer and multiple myeloma. Most preferably, the solid tumor is glioblastoma.

The term "glioblastoma" or "glioblastoma multiforme" refers to a primary brain tumor involving glial cells. Glioblastoma is, preferably, diagnosed based on the histological presence of proliferative glial tumor cells, vascular proliferation and preferentially necrotic tissue areas (for further classification: Louis, D. N., Ohgaki, H., Wiestler, O. D., Cavenee, W. K., Burger, P. C., Jouvet, A., Scheithauer, B. W., and Kleihues, P. 2007. The 2007 WHO classification of tumours of the central nervous system. Acta Neuropathol 114:97-109.)

In a more preferred embodiment of the present invent, the glioblastoma is selected from the group consisting of primary glioblastoma, secondary glioblastoma, de novo glioblastoma, recurrent glioblastoma, glioblastoma with increased methylation of the promoter of the gene $O^6$-Methylguanin-Methyltransferase (MGMT), glioblastoma without increased methylation of the promoter of MGMT, glioblastoma with mutated p53, glioblastoma without mutated p53, glioblastoma with alterations of the gene encoding kappa light polypeptide gene enhancer in B-cells inhibitor (NFKBIA), glioblastoma without alterations of the gene encoding NFKBIA, glioblastoma with alterations of the gene encoding epidermal growth factor receptor (EGFR), glioblastoma without alterations of the gene encoding EGFR, glioblastoma with alterations of the gene encoding platelet-derived growth factor receptor (PDGFRA), glioblastoma without alterations of the gene encoding PDGFRA, glioblastoma with alterations of the gene encoding isocitrate dehydrogenase 1 (IDHI), glioblastoma without alterations of the gene encoding IDHI, glioblastoma with alterations of the gene encoding neurofibromatosis type 1 (NF1) and glioblastoma without alterations of the gene encoding NF1.

The term "alterations" refers to mutations, deletions and the presence of additional copies of the gene in question. Mutations and deletions may be homo- or heterozygous. Moreover, the term "glioblastoma" refers to primary as well as recurrent disease.

Particularly preferred is the treatment of a solid tumor, in particular a solid tumor selected from the group consisting of glioblastoma, Hodkin's lymphoma, colorectal cancer, melanoma hepatocellular carcinoma, breast cancer and multiple myeloma, wherein said tumor is characterized by underexpression of NFKBIA, with a compound as defined by formula I, II or III in combination with an alkylating agent. Preferably, said underexpression of NFKBIA is caused by a heterozygous deletion of the NFKBIA locus (NFKBIA$^{+/-}$) at 14q13.

The compound according to formula I, II or III and the alkylating agent are, preferably, administered simultaneously or subsequently.

The term "simultaneously" refers to the administration of dosages of both compounds which is not separated by more than 5 minutes, more than 10 minutes or more than 20 minutes. More preferably, both compounds are components comprised by a single pharmaceutical composition which is administered to the patient.

The term "subsequent administration" refers to an administration regimen where the interval between the administration of both compounds is chosen to enable or, more preferably, maximize the synergistic effect of the combination. Preferably, the interval between the administration of the compound according to formula I, II or III and the alkylating agent is chosen to achieve simultaneous peak plasma levels of both substances. Also preferably, the interval between the administration of the compound according to formula I, II or III and the alkylating agent does not exceed 1 day, 3 days, 6 days or 9 days.

The administered amounts of compounds are, preferably chosen so that defined ratios of the active compounds at the site of the tumor are achieved. It is known to the person skilled in the art that the effective concentration of a pharmaceutical compound at the site of a tumor depends on the route of administration, the distribution of the compound in different compartments (e.g. blood and tissue), the enzymatic activation of a prodrug and/or the enzymatic inactivation of the active compound, and the rate of excretion of the compound from the body. Thus, the decision about a suitable dosage depends on the aforementioned parameters. However, the person skilled in the art is well aware of this issue and pharmacokinetic analysis helps in determining a dosage of a compound which leads to the desired concentration of the active compound at the site of the tumor.

Preferred routes of administration are oral, intravenous, intrathecal intraparenchymal administration.

Preferably, at the site of the tumor the molar ratio of niclosamide (expressed as mol % of the added molar concentrations of niclosamide and temozolomide) is 10 mol %, 20 mol %, 30 mol %, 40 mol %, 50 mol %, 60 mol %, 70 mol %, 80 mol % or 90 mol %. More preferably, the molar ratio of both compounds depends on the expression status of NFKBIA.

If the tumor in question is characterized by a decreased expression of NFKBIA, the molar ratio of niclosamide is, preferably, equal to or larger than 40% of the added molar concentrations of niclosamide and temozolomide. More preferably, the concentration is larger than 50 mol %, larger than 60 mol %, larger than 70 mol %, larger than 80 mol % or larger than 90 mol %, most preferably it is 50 mol %.

If the tumor in question is not characterized by a decreased expression of NFKBIA, the molar ratio of niclosamide is, preferably, smaller than 40% of the added molar concentrations of niclosamide and temozolomide. More preferably, the concentration is smaller than 40 mol %, smaller than 30 mol %, smaller than 20 mol % or smaller than 10 mol %, most preferably it is 10%.

The term "treating" refers to the administration of the compounds of the present invention to a patient with the aim of restoring or maintaining the patient's health with respect to a solid tumor.

In a preferred embodiment of the present invention, the treatment is curative. Preferably, curative treatment aims at the complete eradication of all tumor cells from the patient's body. It is to be understood that curative treatment may not be successful in all patients receiving the treatment. Almost no medical therapy in general, and almost no cancer therapy in particular, works in each and every patient. However, curative treatment means that a significantly larger portion of patients can be cured as compared to groups patients receiving no treatment or only a placebo. Preferably, the groups of patients receiving no treatment or a placebo ("control groups") have the same characteristics such as age, type and severity of disease, gender or body weight as the group receiving treatment. Statistical methods for determining whether the rate of success is higher in one group of patients as compared to another one are well known to the person skilled in the art.

In another preferred embodiment of the present invention the treatment is palliative. Palliative treatment does not aim at the complete eradication of all tumor cells from the patient's body although such an outcome is not excluded by the term "palliative treatment". Preferably, palliative treatment aims at the reduction of tumor associated symptoms, such as pain or neurological deficiencies, in the patient. Also preferably, palliative treatment aims at decreasing tumor bulk and symptoms associated therewith, increasing the time until tumor progression or increasing the time of survival. Furthermore, it is preferred that "palliative treatment" keeps the tumor stable, i.e. prevents the tumor mass from increasing and the formation of new metastases.

Preferred subtypes are adjuvant or neoadjuvant treatment regimens. Both, adjuvant and neoadjuvant treatment are characterized by the administration of the compounds of the present invention in combination with a surgical removal of one or more solid tumors.

The term "neoadjuvant treatment", preferably, refers to the administration of the compounds of the present invention prior to surgery. Such an administration regimen may be used to reduce the size of the tumor before surgery in order to increase the chance of a complete surgical removal or in order to decrease the amount of tissue that has to be resected during surgery so that surgery is less straining for the patient.

Preferably, the term "adjuvant treatment" refers to the administration of the compounds of the present invention after surgery. Adjuvant treatment may also be accompanied by radiotherapy. In many cases, surgery does not result in the complete resection of the tumor or of all tumors from the patient's body. Distant metastases may be already present but too small to be detected by imaging methods. Similarly, tumor cells may already have spread locally beyond the apparent margins of the tumor. In both cases, adjuvant therapy with the compounds of the present invention offers the chance to kill those tumor cells which are not removed by surgery and—where applicable—radiotherapy, thus improving the chance of a complete cure.

Both, adjuvant as well as neoadjuvant treatment may be administered as curative as well as palliative treatment.

In some cases, a tumor is not amenable to surgery either because the patient is so weak that surgery has to be considered an unacceptable risk or because the tumor is not accessible to surgery without damaging vital anatomical structures of the patient. Both situations frequently occur in patients with metastasized tumors. In such cases the advanced stage of the cancer disease weakens the patient considerably and, at the same time, the many tumors present in the body would require extensive surgery. In these cases it is preferred that the compound according to formula I, II or III alone or in combination with the alkylating agent is administered as systemic treatment without surgery. The person skilled in the art knows that medical treatment of a tumor typically relies on the combination of 2, 3 or even more pharmaceutical compounds. Therefore, the compound according to formula I, II or III alone or the combination of the compound according to formula I, II or III and the alkylating agent may be complemented with further cytostatic and/or cytotoxic compounds.

In yet another preferred embodiment of the present invention, the compounds of the present invention the treatment aims at preventing recurrence of an apparently successfully treated tumor. Frequently, treatment of a tumor by means of surgery, radiation therapy, chemotherapy or a combination of any of the aforementioned therapies induces a remission of the tumor. Remission of a tumor is a state, where no traces of a tumor are detectable clinically, e.g. by imaging methods, visual inspection or laboratory parameters. However, in many cases tumors recur at the same location as the original tumor(s) or at distant body parts within a few years after apparently successful treatment. Therefore, remission of a tumor does not equal a successful cure. The compounds of the present invention may be administered in order to prevent recurrence of an apparently successfully treated tumor independent of the primary therapy chosen.

The patient is, preferably, a vertebrate, more preferably, a mammal. Even more preferably, the patient is a cat, dog, monkey, sheep, goat, pig, mouse, rat or human. Most preferably, the patient is a human.

In an embodiment of the present invention, the compounds outlined above are present as pharmaceutically acceptable salts. The term "pharmaceutically acceptable salt" refers to a salt of the compound of the present invention. Suitable pharmaceutically acceptable salts of the compound of the present invention include acid addition salts which may, for example, be formed by mixing a solution of the compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound of the invention carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of general formula (I)-(III). A prodrug is a pharmacologically active or inactive compound that is modified chemically through in vivo physiological action, such as hydrolysis, metabolism and the like, into a compound of this invention following administration of the prodrug to a patient. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme. The suitability and techniques involved in making and using prodrugs are well known by those skilled in the art. For a general discussion of prodrugs involving esters, see Svensson and Tunek, Drug Metabolism Reviews 16.5 (1988), and Bundgaard, Design of Prodrugs, Elsevier (1985). Examples of a masked acidic anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 0 039 051 (Sloan and Little, Apr. 11, 1981) discloses Mannich-base hydroxamic acid prodrugs, their preparation and use.

Compounds of the present invention and also the starting materials for their preparation according to the invention can be synthesized as shown herein, and, alternatively, by methods and standard procedures known to those skilled in the art, i. e. as described in the literature (for example in the standard works, such as Houben-Weyl, Methoden der organischen Chemie [Methods of Organic Chemistry], Georg-Thieme-Verlag, Stuttgart), under reaction conditions which are known to those skilled in the art and suitable for the said reactions.

If desired, the starting materials can also be formed in situ by not isolating them from the reaction mixture, but instead immediately converting them further into the compounds of the present invention. On the other hand, it is possible to carry out the reaction stepwise. It should be noted that the general procedures are shown as it relates to preparation of compounds having unspecified stereochemistry. However, such procedures are generally applicable to those compounds of a specific stereochemistry, e.g., where the stereochemistry at a sterogenic center is (S) or (R). In addition, the compounds having one stereochemistry (e.g., (R)) can often be utilized to produce those having opposite stereochemistry (i.e., (S)) using well-known methods, for example, by inversion.

Certain compounds of the present invention can exist in unsolvated forms as well as in solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds. The racemates, enantiomers, diastereomers, geometric isomers and individual isomers are all intended to be encompassed within the scope of the present invention. Accordingly, the compounds of this invention include mixtures of stereoisomers, especially mixtures of enantiomers, as well as purified stereoisomers, especially purified enantiomers, or stereoisomerically enriched mixtures, especially enantiomerically enriched mixtures. Also included within the scope of the invention are the individual isomers of the compounds represented by formulas (I) to (IV) below as well as any wholly or partially equilibrated mixtures thereof. The present invention also covers the individual isomers of the compounds represented by the formulas below as mixtures with isomers thereof in which one or more chiral centers are inverted. Also, it is understood that all tautomers and mixtures of tautomers of the compounds of formulas (I) to (IV) are included within the scope of the compounds of formulas (I) to (IV) and preferably the formulas and sub-formulas corresponding thereto.

Racemates obtained can be resolved into the isomers mechanically or chemically by methods known per se. Diastereomers are preferably formed from the racemic mixture by reaction with an optically active resolving agent.

Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as -camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture.

The diastereomer resolution can also be carried out by standard purification processes, such as, for example, chromatography or fractional crystallization.

It is also possible to obtain optically active compounds of formulas (I) to (IV) by the methods described above by using starting materials which are already optically active.

In a further aspect the present invention relates to a pharmaceutical composition comprising a compound according to formula I, II or III, wherein A and $R_1$ to $R_{11}$ have the meaning and preferred meanings set out above, and a pharmaceutically acceptable excipient for use in treating of a solid tumor. In a preferred embodiment, the pharmaceutical composition additionally comprises an alkylating agent, preferably as defined by formula IV, wherein X, Y, $R_{31}$ and $R_{32}$ have the meaning and preferred meanings set out above.

A "pharmaceutical composition" as referred to in the present application comprises at least one compound of the present invention and at least one pharmaceutically acceptable carrier.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 80%, more preferably from 20% to 70% of the active compound or active compounds. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. Liquid forms are particularly preferred for topical applications to the eye. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In a preferred embodiment of the present invention, the pharmaceutical composition additionally comprises at least one further cytostatic or cytotoxic compound. Said additional compound is selected from the group consisting of Temozolimide, Daunorubicine, Gambogic acid amide, Gambogic acid, Thimerosal, Mitoxanthrone hydrochloride, Phenylmercuric acetate, Dactinomycin, Pristimerin, Epirubicin hydrochloride, Vincristine sulfate, Emetine, Paclitaxel, 10-Hydroxycamptothecin, Doxorubicine, Colchicine, Camptothecin, Teniposide, Vinblastine sulfate, Mitomycin C, Floxuridine, Ouabain, Ancitabine hydrochloride, Quinacrine hydrochloride, Niclosamide, Amsacrine, Thioguanine, Rotenone, Aklavine hydrochloride, Cytarabine, Methotraxate, and Picropodophyllotoxin.

Further preferred additional cytostatic or cytotoxic compounds include anti-estrogens such as faslodex, tamoxifen or raloxifen; any inhibitors of topoisomerase I or II, such as camptothecin (topo I) or etoposide (topo II); any compound that acts through inhibiting aromatase activity, such as anastrozole or letrozole; any preparation that interferes with HER2 signalling such as herceptin; any compound that interchelates DNA, such as doxorubicin. Particularly preferred cytostatic or cytotoxic drugs, which can be combined with the compounds of the present invention are alkylating substances, anti-metabolites, antibiotics, epothilones, nuclear receptor agonists and antagonists, anti-androgenes, anti-estrogens, platinum compounds, hormones and antihormones, interferons and inhibitors of cell cycle-dependent protein kinases (CDKs), inhibitors of cyclooxygenases and/or lipoxygenases, biogeneic fatty acids and fatty acid derivatives, including prostanoids and leukotrienes, inhibitors of protein kinases, inhibitors of protein phosphatases, inhibitors of lipid kinases, platinum coordination complexes, ethyleneimenes, methylmelamines, trazines, *vinca* alkaloids, pyrimidine analogs, purine analogs, alkylsulfonates, folic acid analogs, anthracendiones, substituted urea, methylhydrazin derivatives, in particular acediasulfone, aclarubicine, ambazone, aminoglutethimide, L-asparaginase, azathioprine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin dapsone, daunorubicin, dibrompropamidine, diethylstilbestrole, docetaxel, doxorubicin, enediynes, epirubicin, epothilone B, epothilone D, estramucin phosphate, estrogen, ethinylestradiole, etoposide, flavopiridol, floxuridine, fludarabine, fluorouracil, fluoxymesterone, flutamide fosfestrol, furazolidone, gemcitabine, gonadotropin releasing hormone analog, hexamethylmelamine, hydroxycarbamide, hydroxymethylnitro furantoin, hydroxyprogesteronecaproat, hydroxyurea, idarubicin, idoxuridine, ifosfamide, interferon γ, irinotecan, leuprolide, lomustine, lurtotecan, mafenide sulfate olamide, mechlorethamine, medroxyprogesterone acetate, megastrolacetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, oleomucin, oxolinic acid, pentamidine, pentostatin, phenazopyridine, phthalylsulfathiazole, pipobroman, prednimustine, prednisone, preussin, procarbazine, pyrimethamine, raltitrexed, rapamycin, rofecoxib, rosiglitazone, salazosulfapyridine, scriflavinium chloride, semustine streptozocine, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxazole, co-trimoxazole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, testolactone, testosteronpropionate, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin, or their respective derivatives or analogs thereof.

In a particularly preferred embodiment of the present invention the additional cytostatic or cytotoxic compound is temozolomide.

Salts/Esters

The compounds within the compositions or compounds usable according to the present invention can be present as salts or esters, in particular pharmaceutically acceptable salts or esters. Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Isotopes

The compounds of the present invention may also contain unnatural proportions of atomic isotopes at one or more of the atoms that constitute such compounds. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^3H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

All isotopic variations of the compounds and compositions of the present invention, whether radioactive or not, are intended to be encompassed within the scope of the present invention.

Solvates

The present invention also includes solvate forms of the compounds within the compositions or compounds according to any of general formulas (I) through (III) usable according to the present invention. The terms used in the claims encompass these forms.

Polymorphs

The invention furthermore relates to compounds within the compositions of the present invention or compounds according to formula (I) usable according to the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

A compound according to the invention can be administered by various well known routes, including oral, rectal, intragastrical, intracranial and parenteral administration, e.g. intravenous, intramuscular, intranasal, intradermal, subcutaneous, and similar administration routes. Parenteral administration and particular intravenous administration, preferably by depot injection, is preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a tablet, a capsule, a capslet, lozenge, a liposome, a suppository, a plaster, a band-aid, a retard capsule, a powder, or a slow release formulation. Preferably the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectable use and include sterile aqueous solutions or dispersions and sterile powders for the extemporaneous preparation of sterile injectable solutions or dispersion. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Besides the preferred excipients mentioned already above, also the following excipients can be chosen, without limitation, to be used with the various pharmaceutical forms of a compound of the invention:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;

b) lubricants such as magnesium stearate, talc, calcium stearate, zinc stearate, stearic acid, hydrogenated vegetable oil, leucine, glyceride and sodium stearyl fumarates, c) disintegrants such as starches, croscaramellose, sodium methyl cellulose, agar, bentonite, alginic acid, carboxymethyl cellulose, polyvinyl pyrrolidone and the like.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician.

As is known in the art, the pharmaceutically effective amount of a given composition will also depend on the administration route. In general the required amount will be higher, if the administration is through the gastrointestinal tract; e.g. by suppository, rectal, or by an intragastric probe, and lower if the route of administration is parenteral, e.g. intravenous.

Within the meaning of this invention, a combination of substituents or variables is permissible only if such a combination results in a stable or chemically feasible compound. A stable compound or chemically feasible compound is one that is not substantially altered when kept at a temperature of 40° C. or less, in the absence of moisture or other chemically reactive conditions, for at least a week. This invention also envisions the quaternization of any basic nitrogen-containing groups of the compounds disclosed herein. Water or oil-soluble or dispersible products may be obtained by such quaternization.

Preferably, the compounds are formulated for oral, intravenous, intrathecal intraparenchymal administration. As both the compounds defined by formulas I, II and III and temozolomide can be administered orally, it is especially preferred that both compounds are formulated for oral administration. In this case, appropriate amounts of both compounds can easily combined for simultaneous administration so that the most effective concentrations are achieved simultaneously at the site of the tumor.

In the most preferred embodiment of the present invention, the compounds of formulas (I) to (IV) are formulated for resorption into the central nervous system.

In another aspect, the present invention relates to a compound according to formula I, II or III, wherein $R_1$ to $R_{11}$ and $R_{21}$ to $R_{27}$ have the meaning as defined above for use in treating of a solid tumor characterized by a decreased expression level of NFKBIA.

Unless indicated otherwise, all definitions given above also apply to this aspect of the invention.

The NF-κB pathway is thought to play an important role in tumorigenesis and in the resistance of tumor cell to chemotherapeutic agents. As set forth above, NFKBIA binds to nuclear factor kappa B in the cytosol, thus inhibiting the translocation of NF-κB into the nucleus. In the study underlying the present invention is has been surprisingly found that niclosamide does not increase the expression of NFKBIA in tumor cells with two intact copies of the gene while it significantly increases the expression of NFKBIA in cells with a heterozygous deletion of the gene encoding NFKBIA.

Thus, niclosamide is particularly suited for the treatment of solid tumors characterized by decreased expression of NFKBIA, in particular by decreased expression caused by a heterozygous deletion of the gene encoding NFKBIA. The tumor may be any tumor recited above provided that it displays a decreased expression of NFKBIA. Preferably, the tumor is selected from the group consisting of glioblastoma, Hodkin's lymphoma, colorectal cancer, melanoma hepatocellular carcinoma, breast cancer and multiple myeloma. Most preferably, the solid tumor is glioblastoma.

In a preferred embodiment of this aspect of the invention, the compound according to formula (I), (II) or (III) is combined with any cytostatic or cytotoxic compound recited above in the present application. Said combination is not limited to alkylating agents.

A preferred embodiment of this aspect of the invention relates to a pharmaceutical composition comprising a compound according to formula I, II or III, wherein $R_1$ to $R_{11}$ and $R_{21}$ to $R_{27}$ have the meaning as defined above and a pharmaceutically acceptable excipient for use in treating of a solid tumor characterized by decreased expression of NFKBIA.

In another aspect, the present invention relates to a method for determining if combination therapy with the cytostatic compound according to formula I, II or III and an alkylating agent is suitable for treating a patient with a solid tumor comprising the steps of
a) determining the expression level of NFKBIA in a sample of tumor cells or tumor tissue of the patient;
b) comparing the determined expression level with a reference value;
c) determining if the combination therapy with niclosamide and an alkylating agent is suitable for the patient based on the result of the comparison of step b), wherein underexpression or a deletion of NFKBIA indicates that the combination therapy is suitable for the patient.

In another aspect, the present invention relates to a method for determining if therapy with the cytostatic compound according to formula I, II or III as defined above is suitable for treating a patient with a solid tumor comprising the steps of
a) determining the expression level of NFKBIA in a sample of tumor cells or tumor tissue of the patient;
b) comparing the determined expression level with a reference value;
c) determining if the therapy with niclosamide is suitable for the patient based on the result of the comparison of step b), wherein underexpression or a deletion of NFKBIA indicates that the combination therapy is suitable for the patient.

Preferably, the method of the invention is performed in vitro. Preferably, the patient suffers from a solid tumor as defined above. More preferably, the patient suffers from glioblastoma.

The sample is, preferably, a sample taken from the patient in question which comprises tumor cells or consists of tumor cells. Such samples can be taken e.g. by biopsy. A sample comprising other cells in addition to tumor cells may be pre-treated in order to increase the fraction of tumor cells in the sample.

Methods for determining the expression level of a gene are well known to the person skilled in the art. Gene expression can be determined by measuring the amount of mRNA-transcripts of the gene in question and it can also be determined by measuring the amount of the protein encoded by the gene. Preferred methods based on the measurement of the amount of mRNA-transcripts generated include quantitative real-time PCR and hybridization-based techniques such as microarrays. Preferred methods for the measurement of the amount of a specific protein include immunological methods such as the enzyme-linked immunosorbent assay (ELISA).

Underexpression is, preferably, defined by comparing the expression level determined in the sample in question with a specific method with the expression level determined in a reference sample or a group of reference samples with the same method. A preferred reference sample is a solid tumor with two intact copies of the gene encoding NFKBIA. Preferably, the promoter regions of both copies of the gene in said tumors do not comprise any mutations.

In a preferred embodiment of the present invention, underexpression of NFKBIA is caused by a heterzygous deletion of the NFKBIA locus (NFKBIA+/−) at 14q13.

In another preferred embodiment of the invention, both copies of the gene encoding NFKBIA are present, but at least one of these copies has an impaired function. A copy has an "impaired function" as understood in the present application if it does not encode a gene product, which has the same function and activity as the gene product encoded by the wildtype. NFKBIA has the ability to bind to nuclear factor kappa B (NF-κB) in the cytosol. As long as it is bound to NF-κB, NF-κB cannot enter the nucleus and function as a regulator of transcription. Thus, the activity of NFKBIA which is most important in the context of the present invention is its binding to NF-κB. Therefore, an "impaired function" as understood by the present application is, most preferably, impaired binding of NFKBIA to NF-κB. This may be caused by exchanges of amino acids crucial for NFKBIA's binding properties for other amino acids or it may be caused by deletions of parts of the gene encoding NFKBIA resulting in a shortened gene product.

A non-functional copy of NFKBIA may result the introduction of a stop-codon or a partial deletion. In this case a shortened gene product is produced which—if lacking crucial functional domains—has a decreased activity.

Non-functional copies may result from point mutations which cause exchanges of amino acids in the gene-product. If said exchange affects a part of the gene product which is important for its function, its activity is decreased or even abolished.

In another aspect, the present invention relates to a method for determining the molar ratio of niclosamide to temozolomide to be administered to a patient with a solid tumor comprising the steps of
a) determining the expression level of NFκBIA in a sample of tumor cells or tumor tissue of the patient;
b) comparing the determined expression level with a reference value;
c) determining the molar ratio of niclosamide to temozolomide based on the result of the comparison of step b), wherein
  (i) an expression above the reference value indicates that the molar ratio shall be below 40% niclosamide; and
  (ii) an expression level below the reference value indicates that the molar ratio shall be equal to or larger than 40% niclosamide.

All definitions given above in this application apply to this aspect of the invention as well.

FIGURE LEGENDS

FIG. 1: Niclosamide effectively inhibits pGBMs cellular viability. (A) Pharmacodynamic analysis of 21 pGBMs (#'s indicated) at day 5 following niclosamide exposure (concentration indicated). Data as mean±SD of triplicates. (B) Spectrum of IC50 values representing the concentrations that decrease the metabolic activity to 50% of control levels. Data collected from three human non-tumor neural cell populations (hnNCs, see Methods), five commercially available glioma/GBM cell lines (see Methods), and the 21 pGBMs (see (A); Table 3). The inset depicts IC50 data from additional pair-wise comparative experiments (symbol coded) on pGBMs derived from tumor center vs. periphery, from primary vs. recurrent disease, from MGMT promoter hypermethylated vs. unmethylated specimens, and from samples with NFKBIA$^{+/+}$ vs. heterozygous NFKBIA deleted genotypes (NFKBIA$^{+/-}$). P-values (***p<0.001) were calculated from comparing hnNCs and GBM cell line data with pGBMs, respectively, using the 1-way ANOVA and Tukey's post hoc tests.

Figure 2:
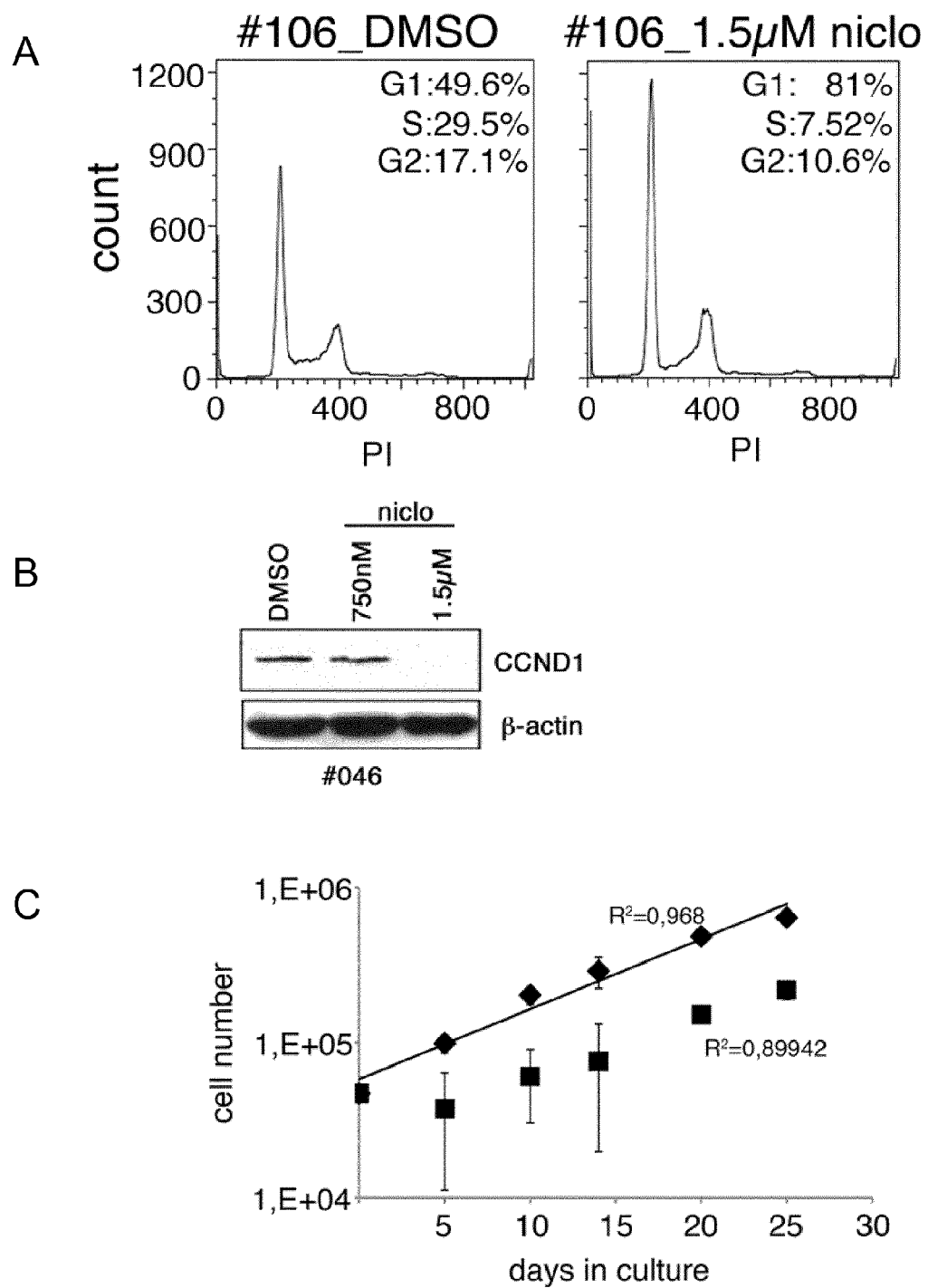
Figure 2:
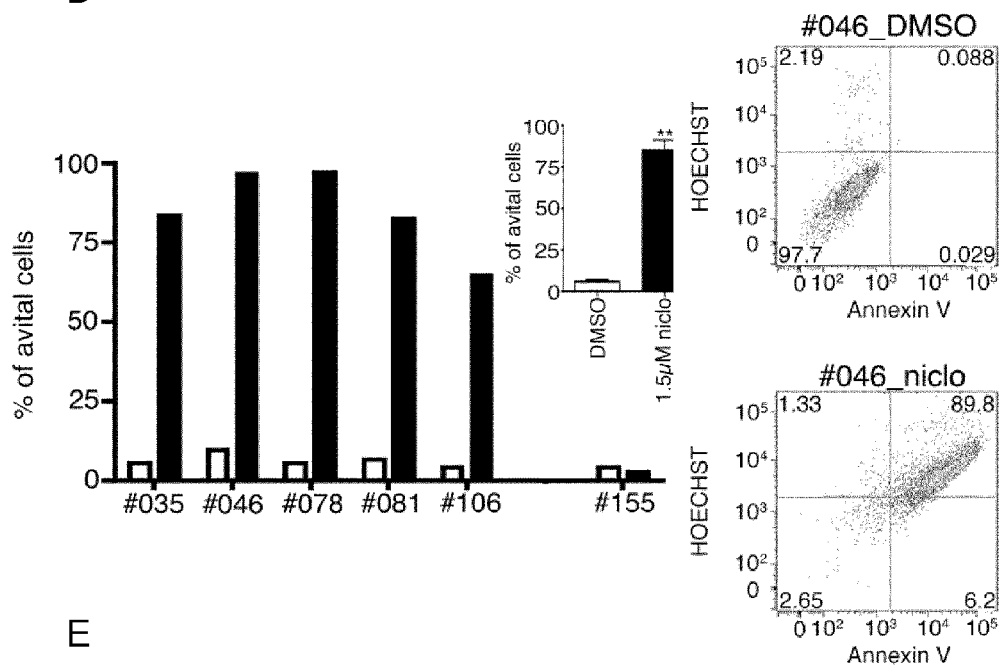
Figure 2:
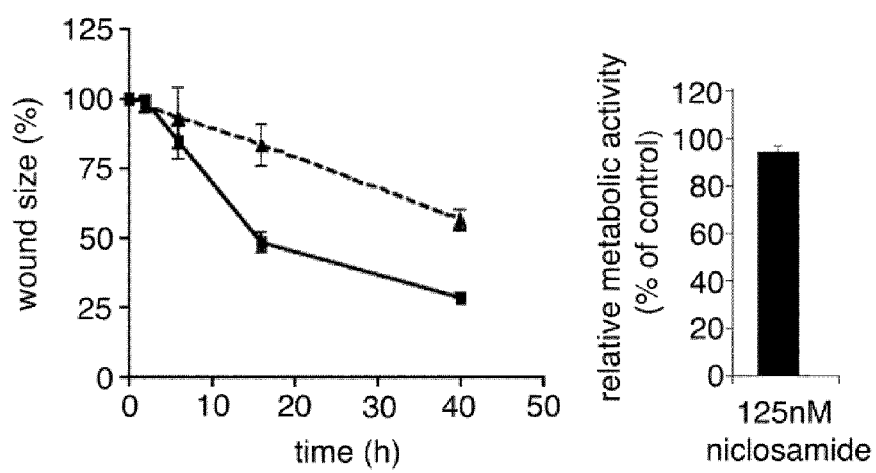

FIG. 2: Niclosamide has cytostatic and cytotoxic effects. (A) Cell cycle analysis at 24 hours post application exposing a strongly increasing G1 peak in the niclosamide (niclo)-treated sample. (B) CYCLIN D1 (CCND1)-western blot of cell extracts derived at this time point. (C) Cellular growth kinetics after a single exposure to niclosamide (1.5 µM; squares) or DMSO (0.01%; rhombi) (pGBM #'s 046, 078, 106; mean data±SD). (D) Graph depicting frequency of avital, i.e. Annexin V$^+$ and/or Hoechst 33258$^+$ cells at 5 days after application of niclosamide (black bars) or 0.01% DMSO (white bars). Inset: mean data (n=5 pGBMs; **p<0.01). Note the lack of pro-apoptotic effects in the non-malignant human cell sample #155. Right inset: representative scatter plots (#046). (E) The scratch assay (n=2 pGBMs) was performed at day two following exposure of 125 nM niclosamide (dotted line) or of 0.0025% DMSO (solid line). The graph exemplifies the time course of scratch closure for case #046 (mean±SD; triplicate analysis).

Figure 3:
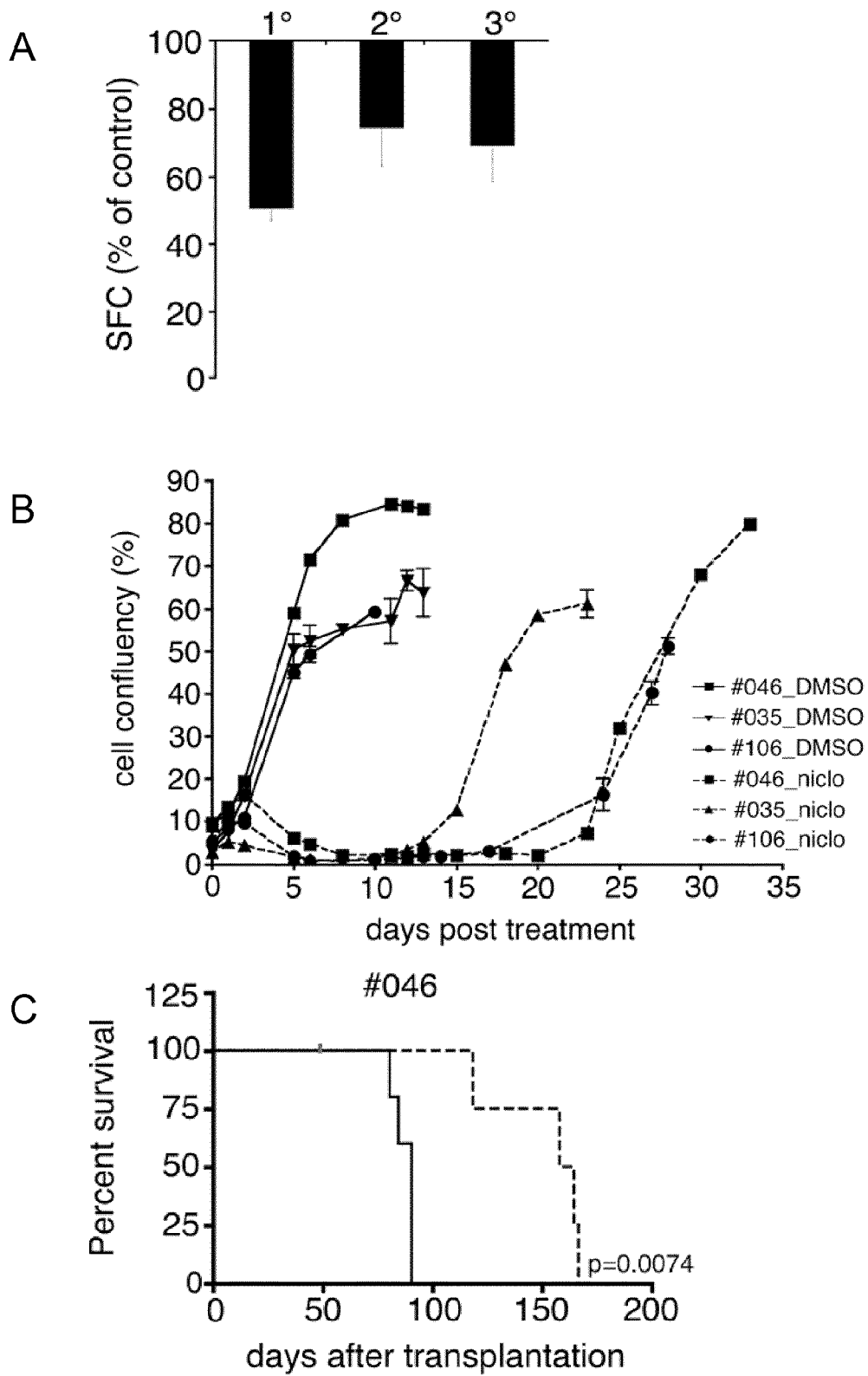

FIG. 3: Niclosamide decreases the tumor-initiating potential of pGBMs. (A) Neurosphere assay (n=4 pGBMs; mean±SD). The graph depicts the relative frequency of primary (1°), secondary (2°) and tertiary (3°) neurospheres from niclosamide pre-treated pGBMs (single exposure). Data show a persistent decrease of sphere-forming cells (SFCs). (B) Long-term cell growth data after single application of 1.5 µM niclosamide (niclo; dotted lines) vs. 0.01% DMSO (solid lines) (mean±SD of triplicate analysis). (C) Kaplan-Meier survival curves of xenografts. For experimentation, pGBM #046 cells were pre-treated with niclosamide (dotted) or DMSO (solid). 10$^6$ vital cells were collected at day 5 and stereotactically injected into the striatum of immunocompromised mice. Distressed animals were euthanized. With one exception (niclosamide; red dot), animals showed intracerebral tumor manifestation.

Figure 4:
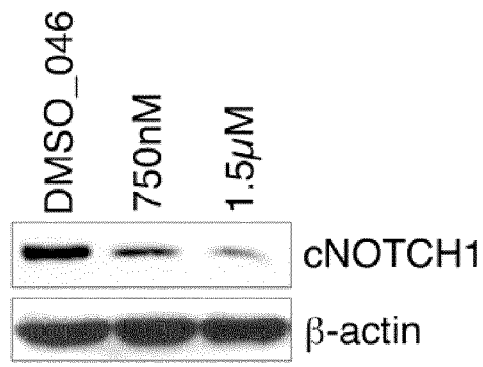
Figure 4:
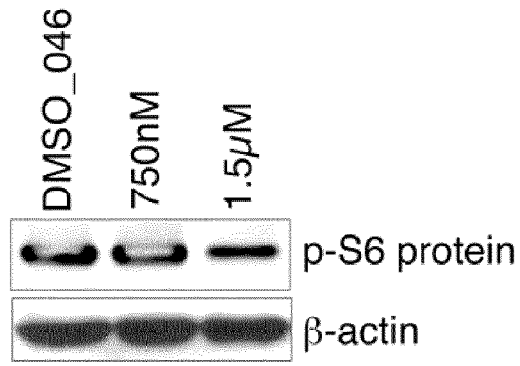
Figure 4:
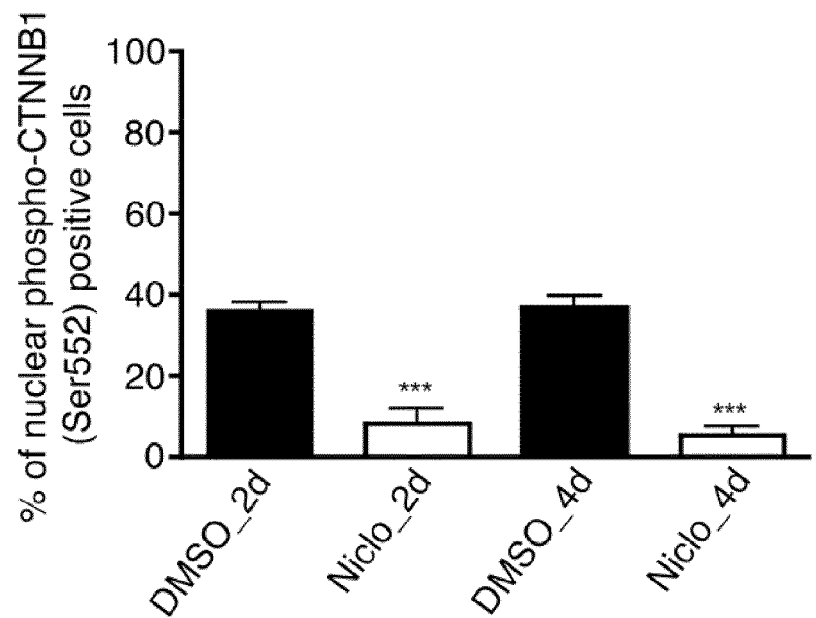
Figure 4:
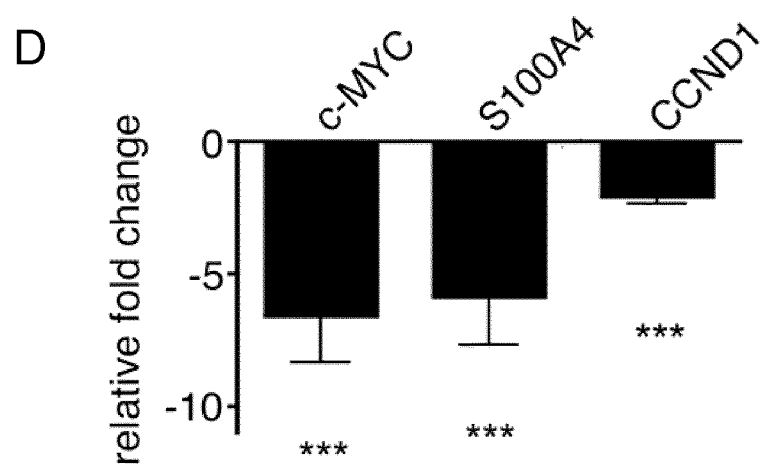

FIG. 4: Niclosamide affects several cancer regulating signaling pathways simultaneously. Western blot analysis of cleaved-NOTCH1 (A) and phospho-S6-protein (B) was performed at 5 days after single dose application. (C) Data quantification reveals a significant decrease of nuclear phospho-CTNNB1 (Ser552)$^+$ cells (*p<0.001, triplicates, mean±SD). (D) qRT-PCR analysis of WNT/CTNNB1 target genes (*p<0.001, triplicates, mean±SD). Expression levels relative to the DMSO control. P-values calculated using 1-way ANOVA analysis with Bonferroni post-test. Note, all experiments conducted with pGBMs #'s 046, 078, 106, and 118.

Figure 5:
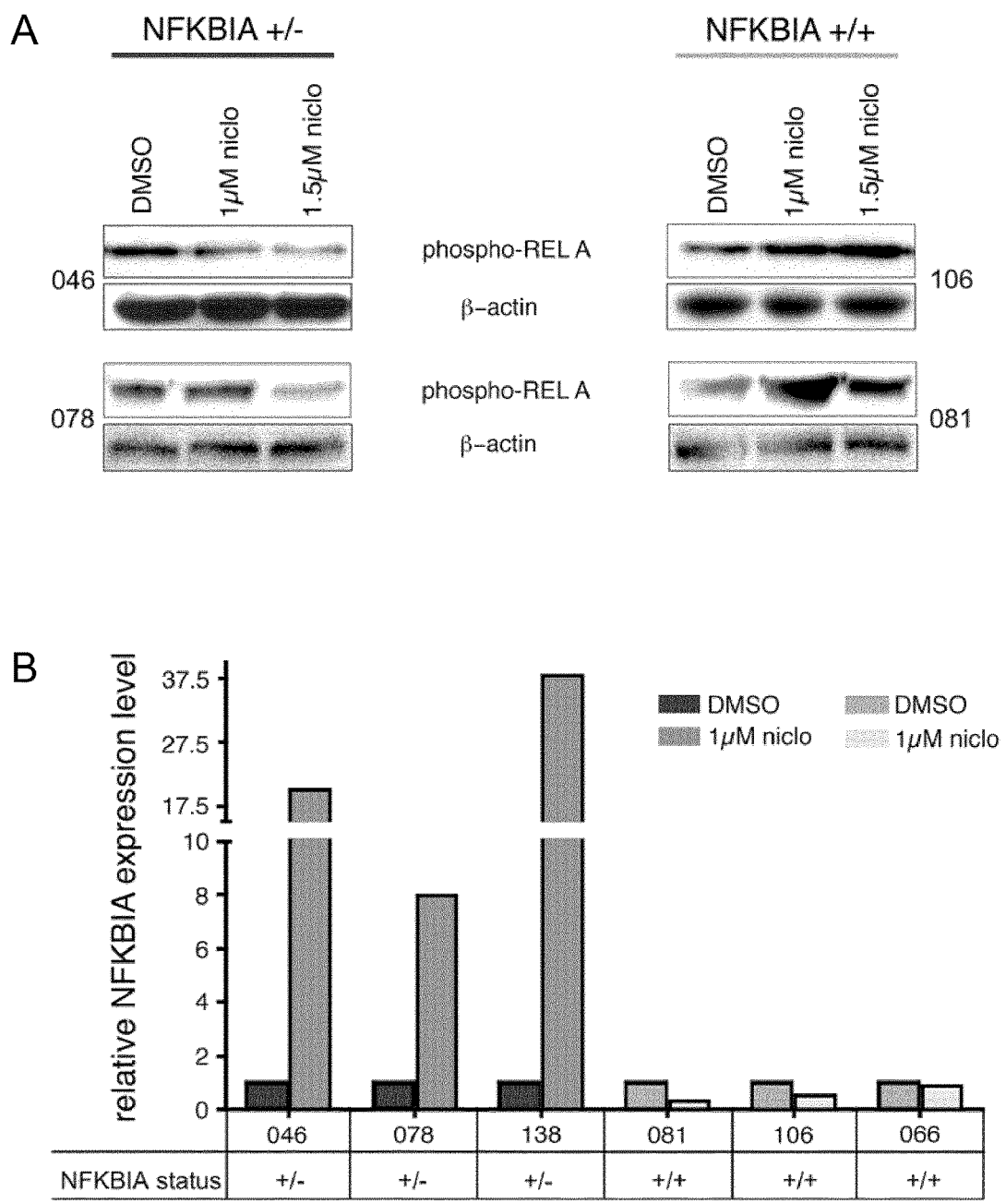
Figure 5:
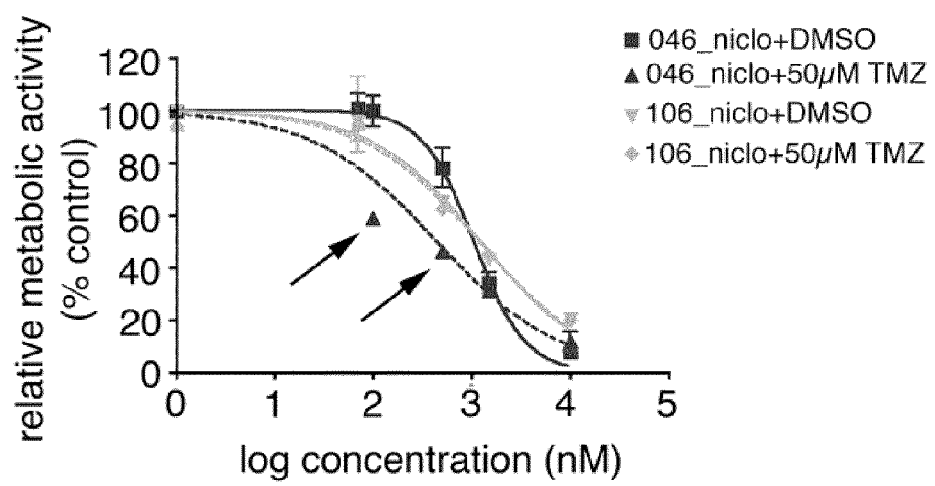

FIG. 5: Deletion and expression level of NFKBIA predicts synergistic activity of niclosamide and TMZ. (A) Western blot analysis of pGBMs with NFKBIA$^{+/-}$ enotype (purple) vs. NFKBIA$^{+/-}$ samples (green). Levels of phospho-RELA (p65-NF-κB) indicating pathway activity were determined 3 days after niclosamide exposure. (B) Quantification of mRNA levels in NFKBIA$^{+/+}$ (046, 078, 138) vs. NFKBIA$^{+/-}$ (081, 106, 066) pGBMs in response to niclosamide (light) or DMSO (dark) exposure. Data presented as relative to DMSO control. Inset depicting base-line mRNA expression levels of NFKBIA. (C) Combinatorial pharmocodynamics of TMZ and niclosamide in NFKBIA$^{+/+}$ (n=4) vs. NFKBIA$^{+/-}$ (n=3) pGBMs. Increasing concentrations of niclosamide were supplied either in combination with 50 µM TMZ or with 0.05% DMSO as control. Data exemplified by #'s 046 (NFKBIA$^{+/-}$, square and triangle) and 106, (NFKBIA$^{+/+}$, inverted triangle and diamond) and presented as mean±SD of triplicates. Arrows highlight synergistic activity for the NFKBIA$^{+/-}$ sample. Note, data for the other investigated pGBMs are listed in Table 2.

Figure 6:
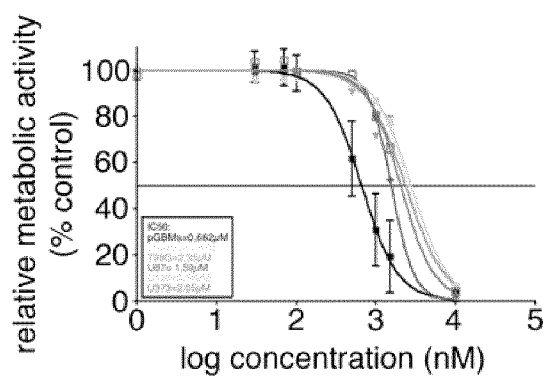
Figure 6:
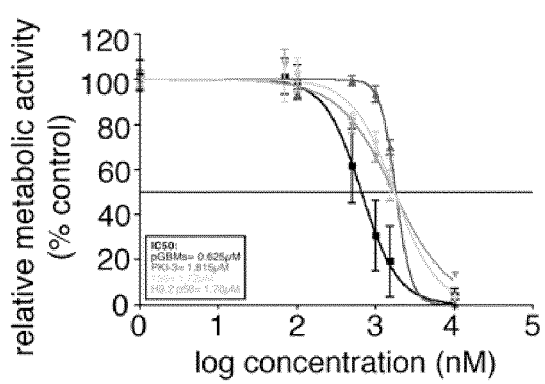
Figure 6:
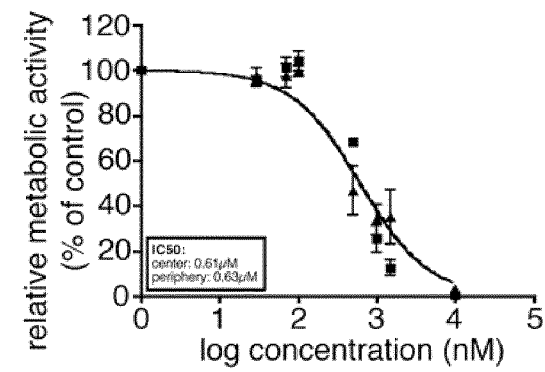
Figure 6:
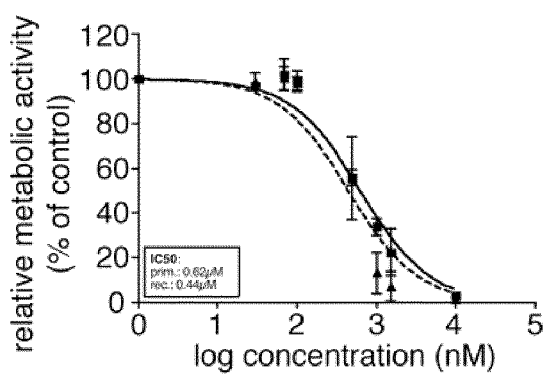
Figure 6:
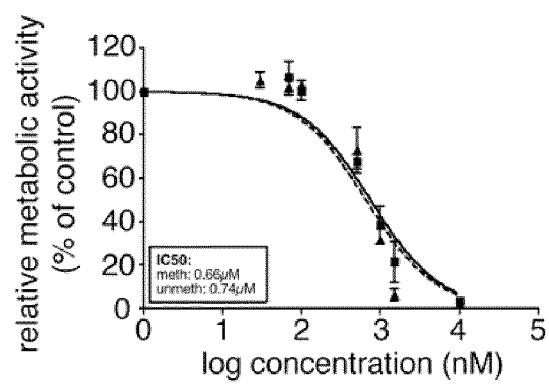
Figure 6:
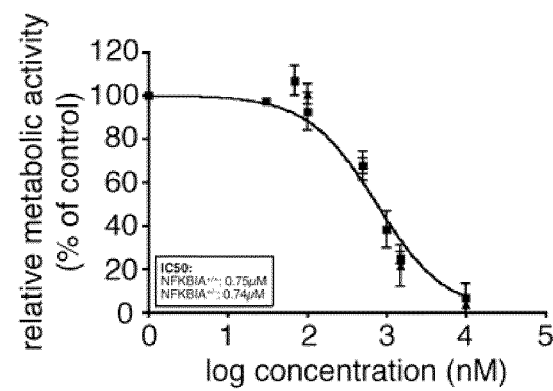

FIG. 6: Niclosamide dose-response curves. The metabolic activity as a measure for cellular viability was determined at 5 days after compound exposure (mean data±SD, triplicate analysis). Data relative to control (DMSO) levels. The IC50 was defined as concentration of niclosamide that reduced the metabolic activity to 50% control levels. (A) Comparison of data for commercially available human glioma/GBM cell lines LN229, T89G, U87, U138, and U272 (grey) vs. 21 pGBMs (black; mean±SD, compare with FIG. 2A). (B) Comparison of data for human non-malignant neural (control) cell samples PKI-3, #155, and H9.2 (grey) vs. 21 pGBMs (black; mean±SD, compare with FIG. 2A). (C) Evaluation of paired samples derived from tumor core (squares) vs. tumor periphery (triangles) for pGBM #'s 046, 066, and 078. (D) Evaluation of paired samples derived from primary disease (squares) vs. recurrent disease (triangles) for pGBM #'s 091, 118, and 132. (E) Comparison of data for MGMT promoter hypermethylated pGBM samples #023 and #025 (triangles) vs. MGMT promoter unmethylated pGBM samples #'s 046, 106, and 138 (squares). (F) Comparison of data for NFKBIA$^{+/+}$ pGBM samples #'s 066, 081, and 106 (squares) vs. NFKBIA$^{+/-}$ pGBM samples #'s 046, 078, and 118 (triangles).

Figure 7:
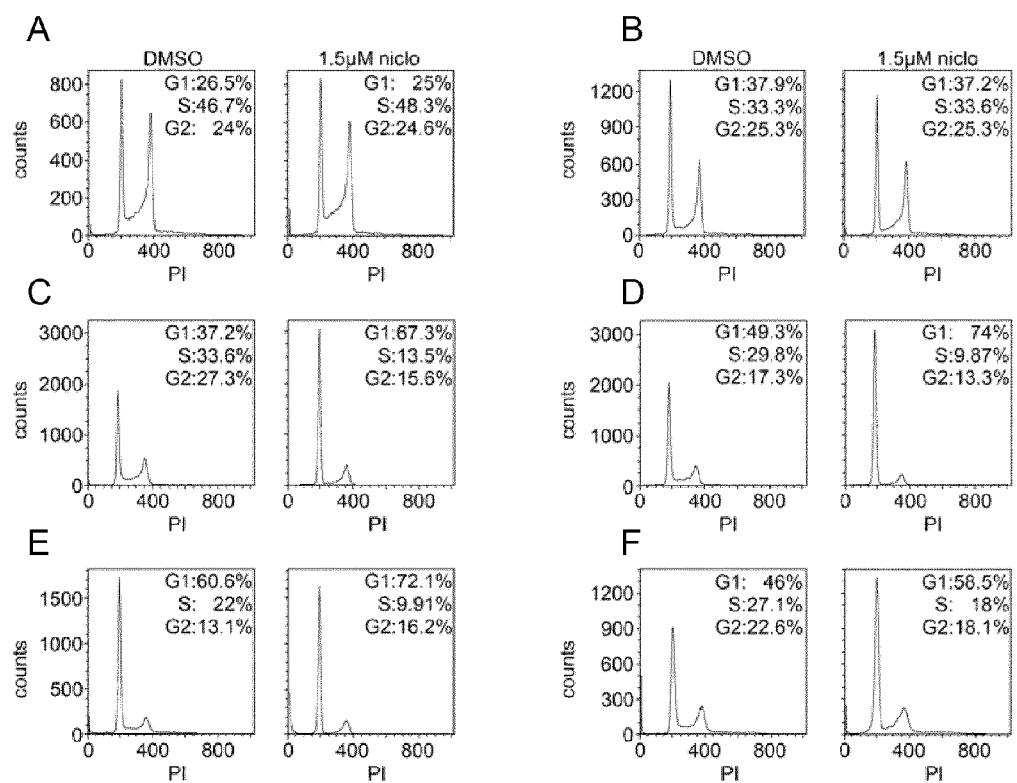

FIG. 7: Niclosamide induces a transient G1 phase arrest in pGBMs. Cell cycle analysis revealed similar results for cases #046 and #106 (PI, propidium-iodide). Shown is #046 exposed to 1.5 µM niclosamide vs. 0.01% DMSO at (A) 6 h, (B) 12 h, (C) 24 h, (D) 48 h, (E) 72 h, and (F) 5 d.

Figure 8:
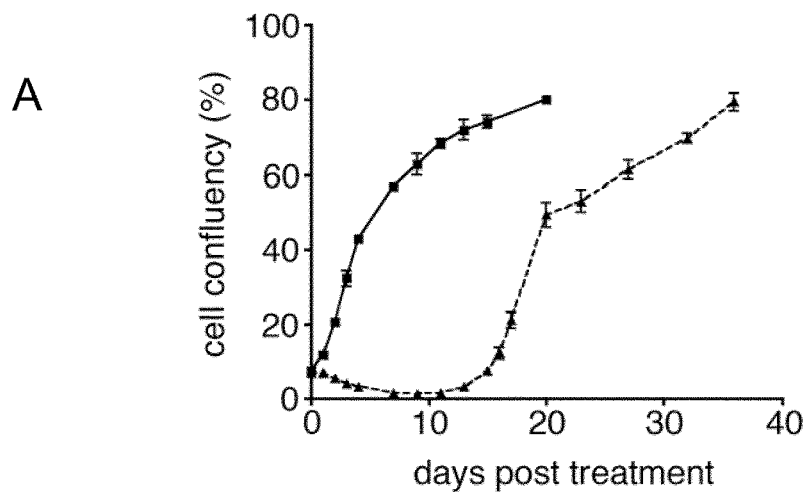
Figure 8:
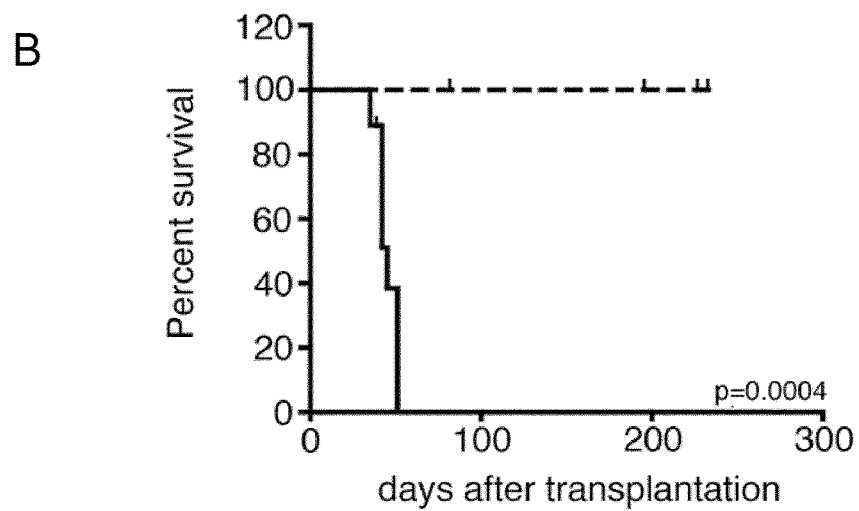
Figure 8:
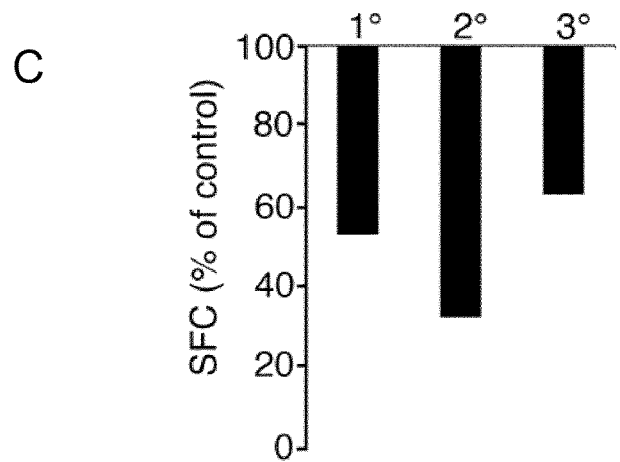

FIG. 8: Niclosamide depletes the tumor-initiating potential of pGBM #GNV019. (A) Long-term cell growth data after single dose niclosamide application (1 µM, dotted) vs. DMSO (0.01%, solid). (B) Xenograft experiments were conducted similar to methods described for FIG. 4C, with the exception that neonatal mice were used as recipients. Kaplan-Meier survival curves depict the course of DMSO pre-treated (solid) vs. niclosamide (dotted) pre-treated cell grafts. Intracerebral tumor manifestation was noted in 8/9 animals from the DMSO control group. In contrast, no animal that received niclosamide pre-treated grafts showed evidence for tumor formation (censored events). Calculation of the p-value based on the log-rank test.

Figure 9:
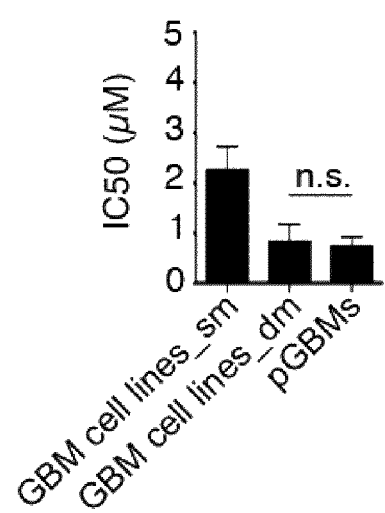

FIG. 9: The graph depicts IC50 data from pharmacodynamic analysis of pGBMs vs. 'standard' glioblastoma (GBM) cell lines. Niclosamide-treated 'standard' cell lines maintained in defined media (dm; n=5; mean±SD) show pGBM-like degrees of sensitivity to niclosamide. P-values were calculated from comparing 'standard' glioblastoma cell line data with pGBMs using one-way ANOVA and Tukey post hoc test. n.s., not significant. (sm; standard media conditions)

Figure 10:
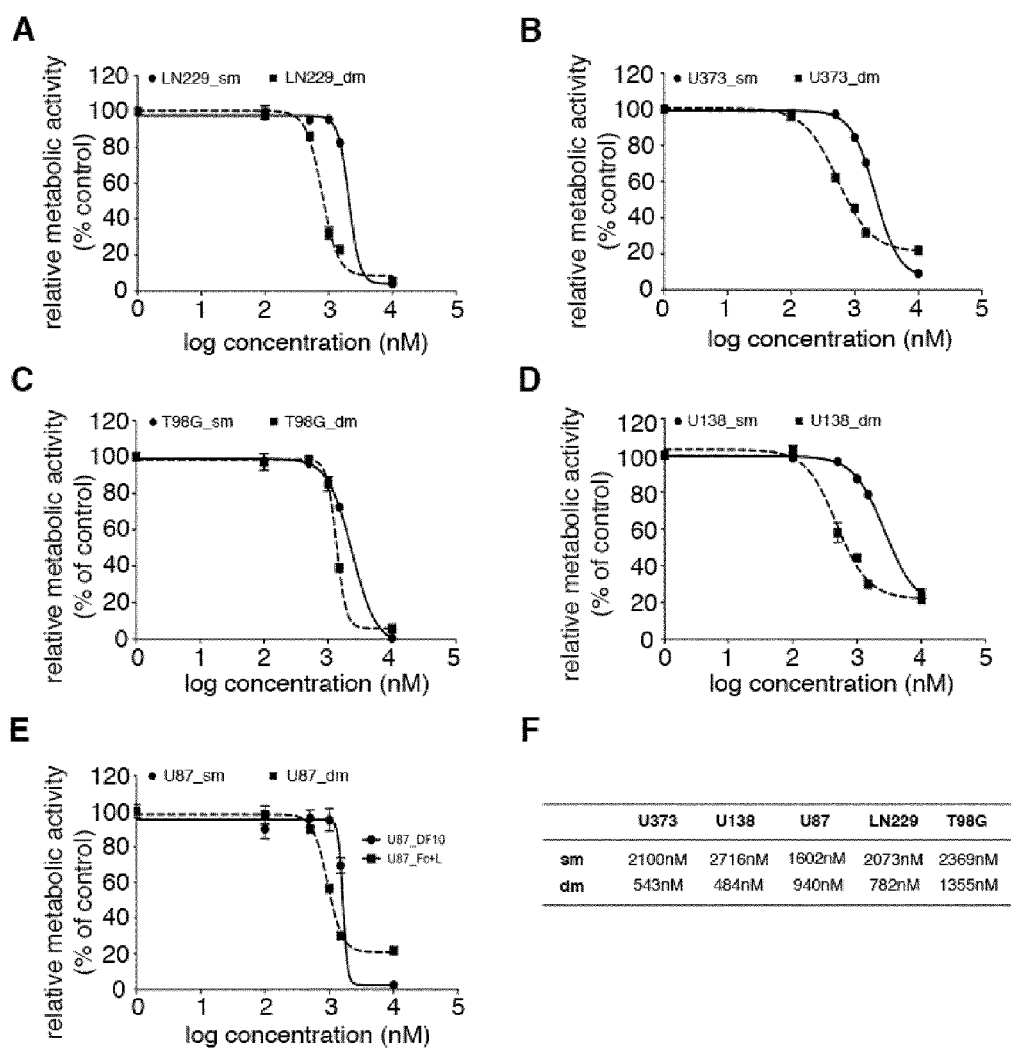

FIG. 10: Niclosamide dose-response curves (A-E), comparison of results obtained from 'standard' GBM cell lines maintained in standard media conditions (sm; solid lines) vs. defined media conditions (dm; dotted lines). It is evident that niclosamide effects are more pronounced (pGBM-like) under dm conditions. (F) Table summarizing the respective IC50 values.

Figure 11:
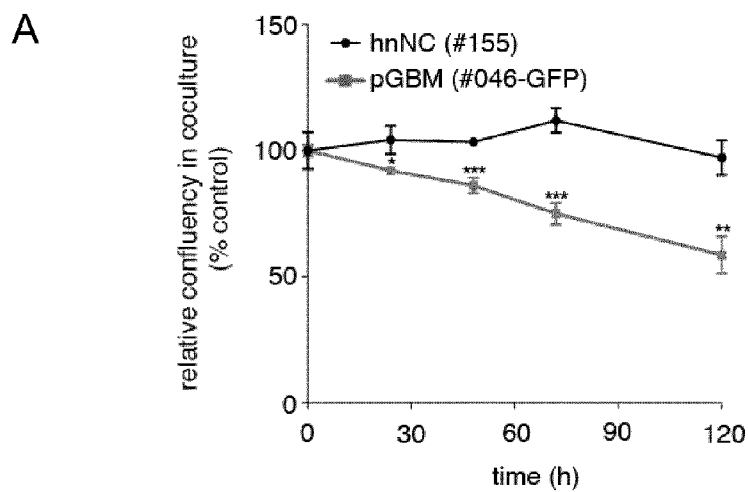
Figure 11:
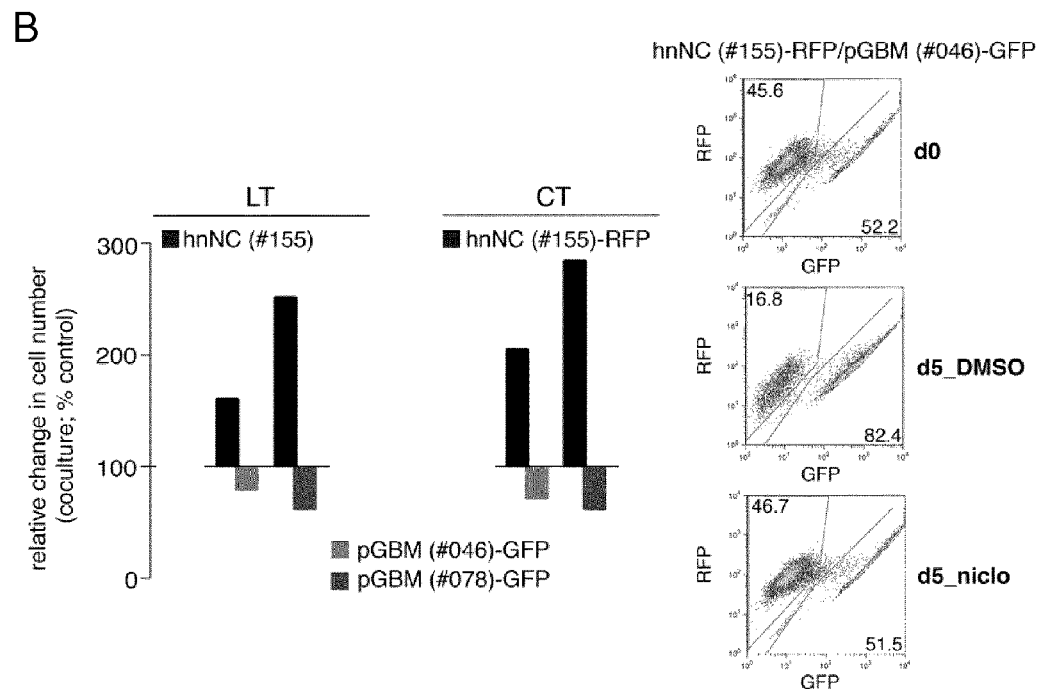

FIG. 11: Coculture experiments combining hnNC case #155 with various pGBMs. (A) CellaVista-based analysis of cocultures. Data were obtained at indicated time points after application of niclosamide (1 µM). Triplicate analysis (*, p<0.001; , p<0.01). (B) FACS data obtained 5 days after the application of niclosamide (1 µM) to respective cocultures. The inset depicts a representative set of scatter plots. Note that pGBMs cases #046 and #078 are NFKBIA+/−; cases #035 and #106 are NFKBIA+/+ genotypes. LT, lentivirally transduced; CT, CellTracker-labeled populations.

Figure 12:
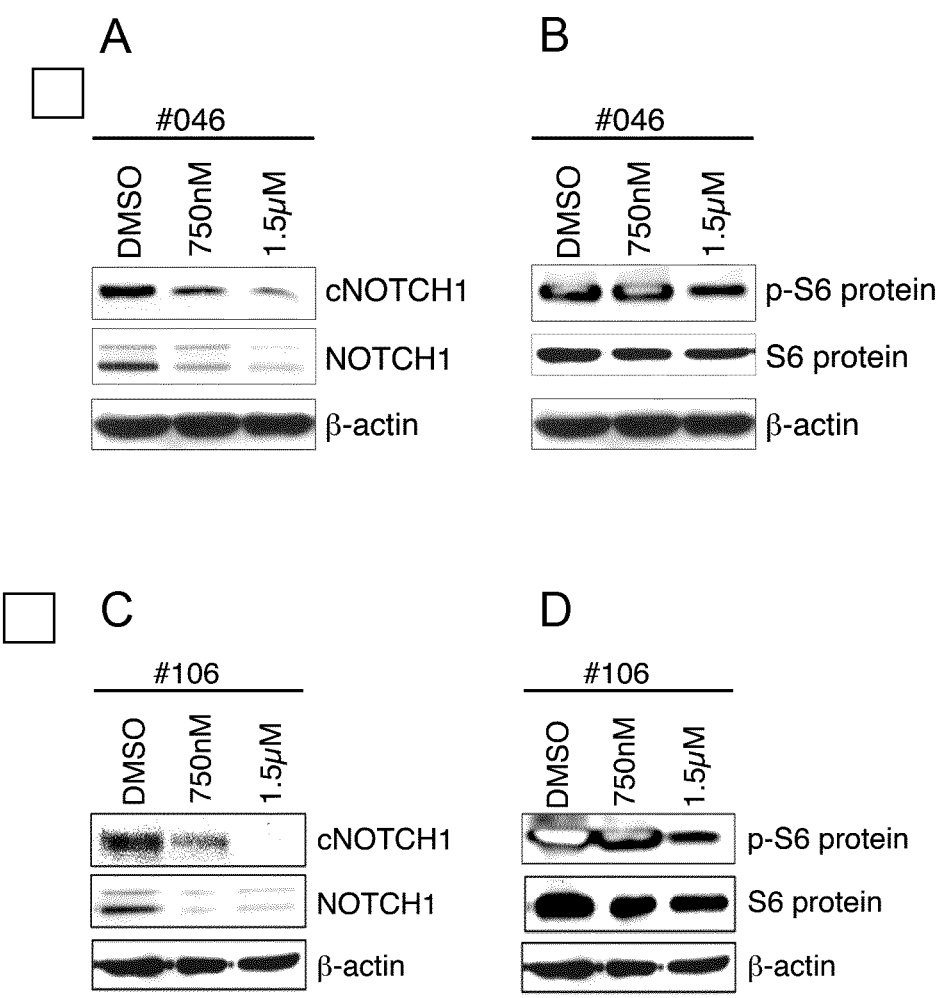

FIG. 12: Niclosamide inhibits NOTCH and mTOR signaling independent of the cellular NFKBIA status (#046=NFKBIA+/−; #106=NFKBIA+/+) (shown here by decreasing levels of phosphorylated S6 protein 5 days after single dose application of ND; n=4 pGBMs analyzed).

Figure 13:
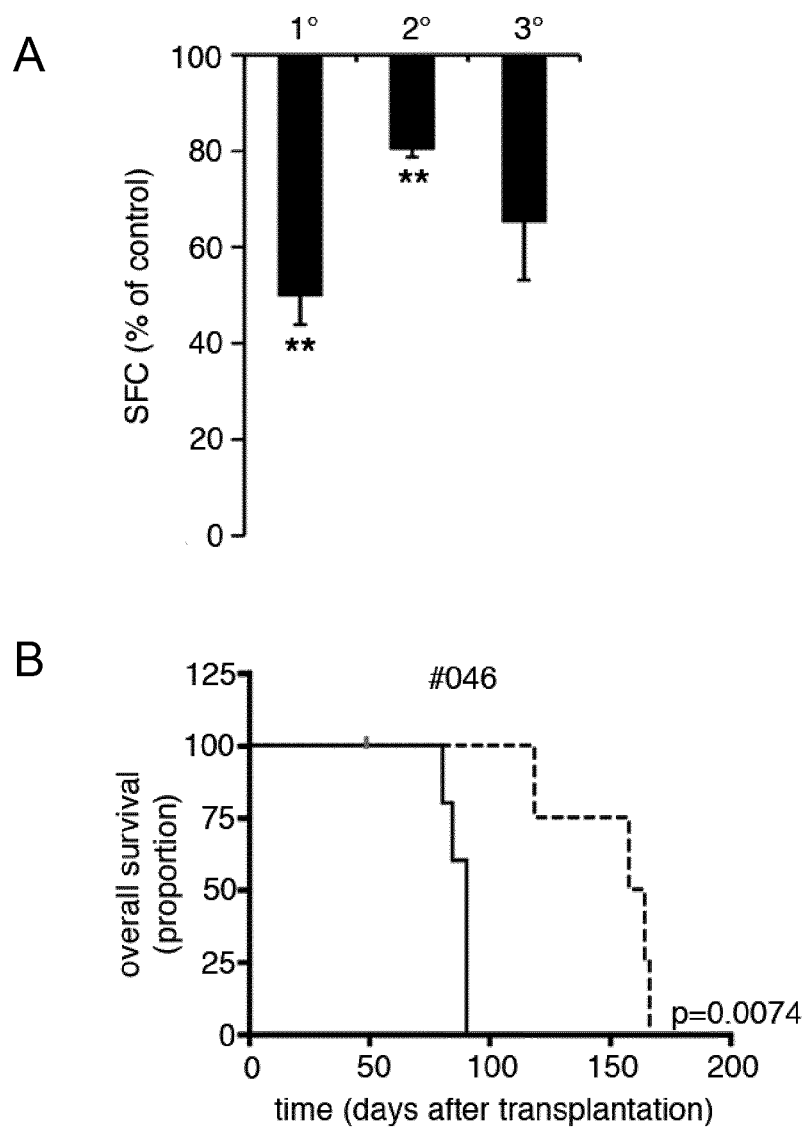

FIG. 13: Niclosamide inhibits the malignant potential of pGBMs (NFKBIA+/− genotypes). (A) Neurosphere assay (n=2 pGBMs in triplicates; mean±SD). The graph depicts the relative frequency of primary (1°), secondary (2°), and tertiary (3°) neurospheres from niclosamide preexposed pGBMs (single exposure). Note the persistent decrease of sphere-forming cells (SFC), p<0.01. (B) Kaplan-Meier survival curves (similar to Additional evidence, FIG. 4**). Intracerebral tumors manifested in all but one animal (niclosamide; red dot).

Figure 14:
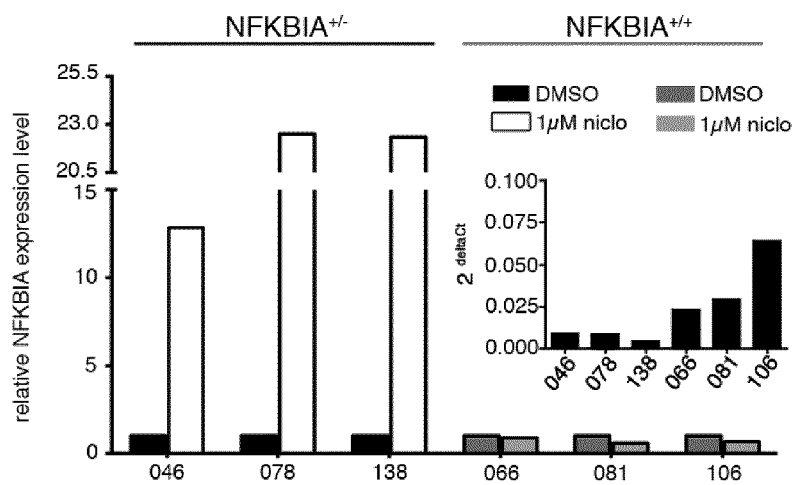
Figure 14:
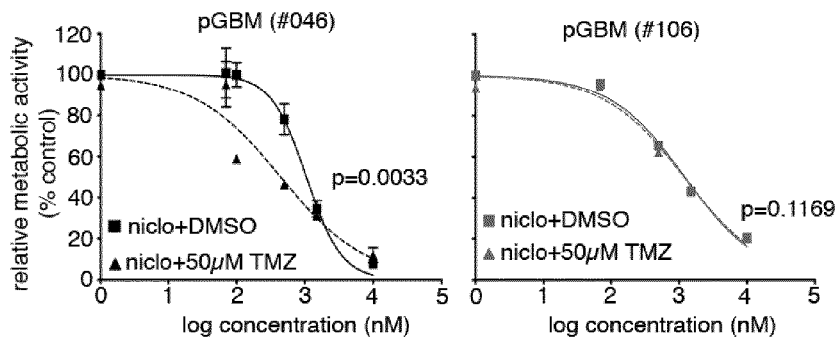

FIG. 14: Deletion and expression level of NFKBIA predicts synergistic activity of niclosamide (Niclo) and temozolomide (TMZ) in pGBMs. (A) Changing mRNA levels in NFKBIA+/+ (gray) versus NFKBIA+/− (black/white) pGBMs in response to niclosamide (relative to DMSO control). Inset, baseline mRNA expression levels of NFKBIA. (B) Combinatorial index (CI) evaluation for application of niclosamide+temozolomide in pGBMs. CIs were expressed as ratio of observed versus expected cell viability. Expected results were calculated according to ref (Chou T C, 2010) as proportion of viable cells after treatment with (only) 1 µM niclosamide multiplied by the proportion of cells following treatment with (only) temozolomide. (CI<1: synergy, CI=1:additive; CI>1:antagonism). (C) Representative combinatorial pharmocodynamics of temozolomide and niclosamide in NFKBIA+/− (left) versus NFKBIA+/+ (right) pGBMs. Increasing concentrations of niclosamide were supplied either in combination with 50 µM temozolomide or with 0.05% DMSO as control. Data presented as mean±SD of triplicates.

Figure 15:
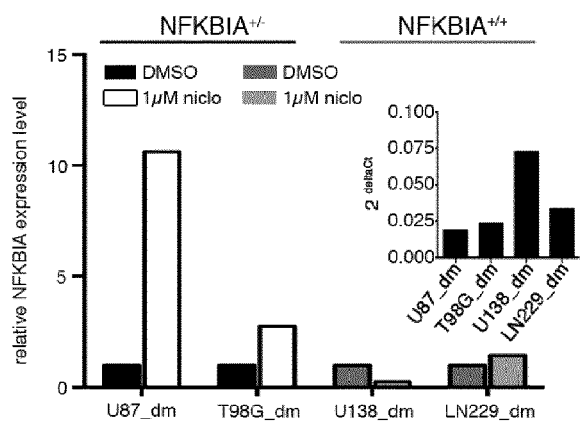
Figure 15:
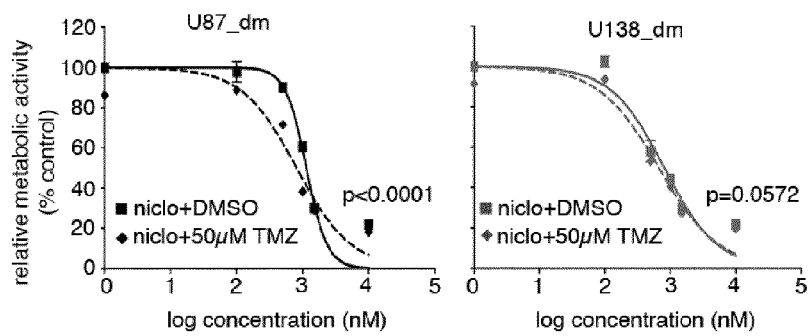

FIG. 15: Deletion and expression level of NFKBIA predicts synergistic activity of niclosamide (Niclo) and temozolomide (TMZ) in standard glioblastoma (GBM) cell lines maintained in defined media conditions (dm). (A) changing mRNA levels in NFKBIA+/+ (gray) versus NFKBIA+/− (black/white) in response to niclo (relative to DMSO control). Inset, baseline mRNA expression levels of NFKBIA. (B) CI evaluation for application of niclo+TMZ. CIs were expressed as ratio of observed versus expected cell viability. Expected results were calculated as proportion of viable cells after treatment with (only) 1 µM niclo multiplied by the proportion of cells following treatment with (only) TMZ. (CI<1:synergy, CI=1:additive; CI>1:antogonism). (C) representative combinatorial pharmocodynamics of TMZ and niclo in NFKBIA+/− (left) versus NFKBIA+/+ (right) standard GBM cell lines. Increasing concentrations of niclo were supplied either in combination with 50 µM TMZ or with 0.05% DMSO as control. Data presented as mean±SD of triplicates. It is evident that the niclo-effects are pGBM-like under dm conditions (compare to FIG. 15).

Figure 16:
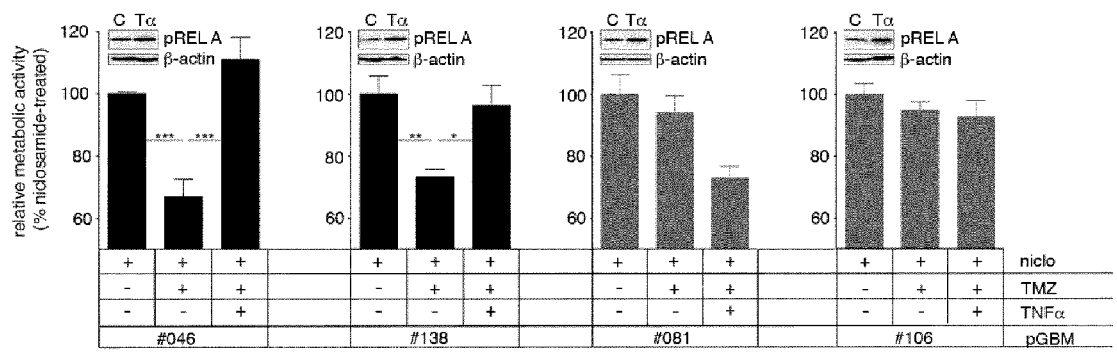

FIG. 16: TNF-a antagonizes synergistic activity in NFK-BIA+/− pGBMs. Graphs present data from combinatorial treatment paradigms in NFKBIA+/− (black) versus NFK-BIA+/+ (gray) pGBMs at 3 days after compound application (niclo, 1 μM; temozolomide, 50 μM; TNF-a, 50 ng/ml). Insets, Western blot analyses of pREL A, indicating NF-kB pathway activity 24 hours after exposure to TNF-a, (Ta; 50 ng/ml) or 0.002% bovine serum albumin (C; control). *$p<0.001$; $p<0.01$; *$p<0.05$ (triplicates; mean±SD; one-way ANOVA and Tukey post hoc tests).

FIG. 17: List of pGBMs and their respective passage numbers used for the various experimental paradigms in this study. (Pharma, pharmacodynamic analysis; CT/LT, co-culture experiments; WB, Western blots).

EXAMPLES

Reagents

The reagents the experiments set out below can be freely purchased, specifically; alamarBlue®, prodidiumiodide, and Hoechst33258 were purchased from Life Technologies; niclosamide and temozolomide were purchased from Sigma-Aldrich; FITC Apoptosis Detection Kit I were purchased from BD Bioscience.

Tissue Samples

Tumor tissue derived from GBM surgery and hippocampus tissue (case #155) derived from epilepsy surgery at the Department of Neurosurgery, University of Bonn Medical Centre. Patient characteristics are detailed in Table 3. pGBM case GNV019 derived from surgery of a 9-year-old boy at the University of Florida Department of Neurosurgery. The local Ethics committees at both sites approved the studies; all patients—or their guardians, provided informed consent. Tissue diagnosis and grading based on the current classification of the World Health Organization (43) and confirmed by two independent neuropathologists at the Department of Neuropathology, University of Bonn Medical Centre (the National Brain Cancer Reference Center).

TABLE 3

Patient data. List of patients and tissue specimens investigated in this study

| Patient | Diagnosis | Sex | Age | Histology | RPA Class | Primary therapy | PFS | OS | MGMTstatus |
|---|---|---|---|---|---|---|---|---|---|
| 021 | new | m | 78 | GBM | V | R, RT/TMZ, 2xTMZ (5/28) | 4 | 12 | unmet |
| 023 | new | f | 79 | GBM | V | RA | NA | 9 | meth |
| 025 | new | m | 70 | GBM | V | R, RTA | NA | NA | meth |
| 035 | new | f | 75 | GBM | IV | RB | 1 | 1 | unmet |
| 046D | new | m | 76 | GBM | IV | RB | 1 | 1 | unmet |
| 066D | new | f | 69 | GBM | IV | R, RT/TMZC | 2 | 2 | unmet |
| 078D | new | m | 52 | GBM | IV | R, RT/TMZ, 2xTMZ (5/28) | 5 | 10+ | unmet |
| 081 | new | w | 86 | GBM | IV | RA | NA | 17 | unmet |
| 091E | new | m | 52 | GBM | IV | R, RT/TMZ, 4xTMZ (5/28) | 7 | 10 | unmet |
| 106 | new | f | 68 | GBM | IV | R, RT/TMZ, 1xTMZ (5/28) | 5 | 5+ | unmet |
| 116 | new | f | 67 | GBM | IV | R, RT/TMZ | 3 | 7 | unmet |
| 118E | new | m | 63 | GBM | IV | R, RT/TMZ, 4xTMZ (5/28) | 7 | 9 | unmet |
| 132E | new | m | 75 | GBM | IV | R, RT/TMZ, 4xTMZ (5/28) | 7 |  | n.d. |
| 135 | new | m | 41 | GBM | IV | R, RT/TMZC | 8 | 9 | n.d. |
| 138 | new | w | 54 | GBM | IV | R, RT/TMZ, 5xTMZ (5/28) | 10 | 14+ | unmet |

A: Patient denied further treatment;
B: Postoperative complications;
C: Discontinuation of therapy due to clinical deterioration;
D: Two pGBM samples were derived from this patient, one from the tumor core (center) and the second from the tumor periphery (see (10));
E: Two pGBM samples were derived from this patient, one at the time of primary disease and the second at the time of disease recurrence;
R: Tumor resection;
RT: Standard radiotherapy;
RT/TMZ: RT plus continuous daily temozolomide (concomitant);
TMZ: Temozolomide (5/28: days 1 to 5 out of a 28-day-cycle)
PFS: Progression-free survival;
OS: Overall survival;
meth: methylated MGMT promoter;
unmet: unmethylated MGMT promoter Mice The Ethical Committee of the University of Bonn, Medical Centre approved all studies involving animals. Rag2$^{-/-}$ Il2rg$^{-/-}$ mice were acquired from Taconic Farm Inc., contractor of the National Institute of Allergy and Infectious Diseases' investigators (42). SCID/Beige mice were purchased from Jackson Laboratory.

Tissue Handling and Culture of Primary Cells

Handling of fresh biopsy samples and derivation of pGBMs (10) and hippocampus tissue-derived AHNPs (#155) (11) were performed as described recently. Media conditions for #GNV019 cells are detailed in (44). Media conditions for all other pGBM and AHNP samples are described in (8). Data were generated from culture passages 7 to 13.

Culture of Established Glioma/GBM Cell Lines

LN229, T98G, U87(MG), U138, and U373(MG) cells were maintained and analyzed in DMEM/F12-based 10% fetal calf serum (Hyclone)-supplemented adherent conditions. These conditions are also referred to as "sm conditions".

Culture of Neural Stem Cells from Human ES and iPS Cells

Together with primary AHNPs (see above), two human long-term self-renewing neural stem cell cultures (lt-NES) were used in this study as non-malignant neural control cells. The lt-NESs were originally derived from the human embryonic stem cell line H9.2 (45) and from the human induced pluripotent stem cell line PKa (46). Conditions for the maintenance of lt-NESs were recently described (45, 47).

For some studies, defined media (dm) were applied to GBM model cell lines for ten days before initiation of experiments. 'dm' resemble media compositions used for the culture of pGBMs and hnNCs/AHNPs, i.e. adapted from (Lee J, Kotliarova S, Kotliarov Y, Li A, Su Q, Donin N M, et al. Tumor stem cells derived from glioblastomas cultured in bFGF and EGF more closely mirror the phenotype and genotype of primary tumors than do serum-cultured cell lines. Cancer Cell 2006; 9(5): 391-403): N2/B27-supplemented Neurobasal™ with addition of growth factors every other day (EGF, bFGF; 10 ng/ml each). Handling of tissue and derivation of pGBMs4, hippocampus-derived AHNPs (#155) (Walton N M, Sutter B M, Chen H X, Chang U, Roper S N, Scheffler B, et al. Derivation and large-scale expansion of multipotent astroglial neural progenitors from adult human brain. Development 2006; 133(18): 3671-81.), and #GNV019 cells (Scheffler B, Walton N M, Lin D D, Goetz A K, Enikolopov G, Roper S N, et al. Phenotypic and functional characterization of adult brain neuropoiesis. Proc Natl Acad Sci USA 2005; 102(26): 9353-8.) were recently described. Data presented here were obtained from short-term expanded pGBMs and AHNPs (passage 5-12; FIG. 18). With exception of the neurosphere assay, all cells were cultured adherently on laminin/poly-L-ornithine coated plastic. In addition to AHNPs, two long-term self-renewing neural stem cell cultures (lt-NES) were used as non-malignant neural control. lt-NESs derived from the human embryonic stem cell line H9.218 and from the human induced pluripotent stem cell line PKa19

Co-Culture Experiments

Lentiviral transduction and selection of pGBMs was conducted using the pLenti6.2/V5-DEST Getaway Vector harboring the coding sequence of GFP as suggested by the manufacturer (Life Technologies). Fluorocytometry confirmed stable cellular expression. Alternatively, pGBMs and hnNCs were labeled with CellTracker™ (-CFSE green fluorescent dye or -Red CMTPX; Life Technologies) according to the manufacturer's instructions. For initiation of respective cocultures, cells were mixed at 1:1 ratios and maintained for 24 hours before conducting experimental paradigms. For distinctive monitoring of cell growth, a fluorescence-enabled CellaVista® System Analyzer (Roche Diagnostics) was used. FACS data for end point analysis were obtained using a FACS calibur flow cytometer (BD Bioscience).

Primary Drug Screening and Pharmacodynamic Analysis

The tested compounds were supplied to cells proliferating in a linear-exponential phase. For all used cell samples, respective titration experiments were conducted before analysis. 24 hours after seeding $2-3\times10^3$ cells/well into laminin/poly-L-ornithine coated 96-well plates, cells were treated with 1 μM of each compound (stock solution 10 mM in DMSO). Control cells were treated with 0.01-0.1% DMSO. Five days after application, metabolic activity as a measure of cell viability was determined using the alamarBlue® assay according to the manufacturers recommendations (Life Technologies). Fluorescence was measured using an Infinite200 microplate reader (Tecan) at $\lambda_{ex}$=540 nm and $\lambda_{em}$=590 nm. Experiments were performed in triplicates for each sample.

For pharmacodynamic analysis, $5\times10^4$ cells were plated in 12-well-plates at 24 hours before application of compound-series and compound combinations, respectively. alamarBlue®-based analysis was conducted at 3-5 days post treatment. Experiments were performed in triplicates. IMC50 was defined as the compound concentration that reduced the metabolic activity by 50% compared to control conditions and determined via data analysis in GraphPad Prism 4.0.

Proliferation Kinetics

Five days post treatment, $4.7\times10^4$ vital cells were plated into 3.5 cm laminin/poly-L-ornithine coated plastic dishes, and four to six days later trypsinized, harvested, counted, and re-plated at a density of $4.7\times10^4$. The procedure was repeated 4-5 times. For long-term monitoring of niclosamide-induced alterations to cellular growth, cell confluence was determined using the CellaVista® system Analyzer (Roche Diagnostics) according to the manufacturer's instructions Cell Migration Analysis $5\times10^4$ cells were plated into 12-well-plates coated with laminin/poly-L-ornithine. Cells were treated with 125 nM niclosamide every 24 hours for 4 days. Three days after plating (at a cell density of 70%), a scratch/wound was inflicted with a sterile pipette tip. Thereafter, culture media was exchanged to remove non-adherent cells. The Plaque Assay application of the CellaVista® system (Roche Diagnostics) was used according to the manufacturer's instructions to monitor the scratch/wound size over time. Triplicate analysis data±SEM.

Cell Cycle Analysis

Cells ($5\times10^4$ per well) were grown in 12-well plates, and collected after treatment at times indicated. Cells were re-suspended in phosphate-buffered saline (PBS), fixed with ice-cold methanol and incubated for a minimum of 24 hours at 4° C. Cell pellets were collected by centrifugation and re-suspended in PBS solution, containing 50 μg/ml propidium iodide and 50 μg/ml RNase. Following incubation for 30 min at 37° C., cells were analyzed for DNA content using a FACS calibur flow cytometer (BD Bioscience).

Annexin V-Based FACS Analysis $1\times10^5$ cells were collected at 5 days following compound application, settled by centrifugation, re-suspended in 100 μl AnnexinV buffer and incubated with 5 μl Annexin V-FITC for 1 hour at room temperature. To distinguish between living and dead cells, labeling with 1.2 μg/ml Hoechst 33258 was used Annexin V presence was determined using standard conditions in a LSRII equipped with FACSDiva Software (BD Bioscience). $2\times10^4$ cells were counted per measurement. The term 'avital cells' was used for Annexin $V^+$–, Annexin $V^+/H33258^+$, and $H33258^+$ cells.

Neurosphere Assay

The neurosphere assay was performed to estimate the frequency of self-renewing clonogenic cells according to established protocols (10, 44). Neurospheres were quantified at 21 days in culture, triturated to a single cell suspension, and re-plated for analysis of the secondary and tertiary neurospheres. Multipotency was determined by plating a representative fraction of 3° neurospheres onto laminin/poly-L-ornithine coated glass coverslips allowing differentiation for 2-3 weeks before fixation in 4% paraformaldehyde (PFA).

Fluorescence Analysis

Immunofluorescence analysis was performed on PFA-fixed samples according to standard protocols (44, 48) using antibodies against βIII tubulin (Promega; monoclonal mouse, 1:1000), GFAP (DAKO, polyclonal rabbit, 1:600), β-catenin, and phospho-β-catenin (Ser552) antibody (both Cell signaling, 1:400). Cell nuclei were visualized with DAPI (Sigma).

Western Blot Analysis

Cell extracts were prepared at 24 to 144 hours following compound application and processed as described (49). Blot membranes were incubated overnight at 4° C. with antibodies against Cyclin-D1 (1:1000; BD Pharmingen), cleaved-Notch1 (1:1000), or phospho-S6 protein (1:1000; all Cell signaling) respectively. After washing, peroxidase-coupled secondary antibodies (Santa Cruz) were added for 1 hour. After washing, blots were developed using the ECL system (Millipore). To confirm equal loading, blots were re-probed with an β-actin antibody (Sigma; 1:5000).

Quantitative Reverse Transcription-Polymerase Chain Reaction (qRT-PCR)

Total RNA was isolated using the RNeasy Mini Kit (Qiagen) according to the manufacturer's instructions. Quantification of RNA concentration was performed with Nanodrop (Peqlab) and 400 ng total RNA was reversely transcribed with oligo-dT primers in a reaction mix (1×RT-Puffer, 10 mM DTT, 500 µM pooled dNTPs, 1 U/µl RNase inhibitor, 2.5 U/µl Expand Reverse Transcriptase; all from Roche Diagnostics). Reaction occurred at 42° C. for 1 h. The cDNA product was amplified in a total volume of 10 µl in 96 well plates using the realplex 4 Mastercylcer Epp Gradient S (Eppendorf) and the following PCR conditions: 95° C. for 2 minutes, followed by 40 cycles of 95° C. for 15 seconds, 60° C. for 20 seconds and 72° C. for 30 seconds. For quantification, the following primers were used:

```
S100A4 forward:
                                      (SEQ ID NO: 1)
5'-CTCAGCGCTTCTTCTTTC-3';

S100A4 reverse:
                                      (SEQ ID NO: 2)
5'-GGGTCAGCAGCTCCTTTA-3';

c-Myc forward:
                                      (SEQ ID NO: 3)
5'-TTCGGGTAGTGGAA-AACCAG-3;

c-Myc reverse:
                                      (SEQ ID NO: 4)
5'-CAGCAGCTCGAATTTCTTCC-3';

Cyclin D1 forward:
                                      (SEQ ID NO: 5)
5'-CCGTCCATGCGGAAGATC-3';

Cyclin D1 reverse:
                                      (SEQ ID NO: 6)
5'-ATGGCCAGCGGGAAGAC-3';

NFKBIA forward:
                                      (SEQ ID NO: 7)
5'-ACACCAGGTCAGGATTTTGC-3';
```

```
NFKBIA reverse:
                                      (SEQ ID NO: 8)
5'-GCTGATGTCAATGCTCAGGA-3.
```

For cDNA quantification of the house keeping gene glycerinaldehyd-3-phosphat-dehydrogenase (GAPDH) the following primers were used: forward: 5'-TGCACCAC-CAACTGCTTAGC-3 (SEQ ID NO: 9); reverse: 5'-GGCATGGACTGTGGTCATGAG-3' (SEQ ID NO: 10). Data analysis was performed with the Mastercycler Epp Realplex Software (Eppendorf). Mean values were calculated from triplicate qRT-PCR reactions. Each mean value of the expressed gene was normalized to the respective mean amount of the GAPDH cDNA.

Single Nucleotide Polymorphism Array Analysis (SNP)

For evaluation of the NFKBIA locus whole-genome genotyping analysis was performed. Genotyping of 299,140 SNPs was conducted using the Illumina HUMANCytoSNP-12 v2.1 according to the manufacturer's Infinium HD assay (Illumina, San Diego, USA). Data was analyzed with Illumina GenomeStudio (2011.1) software including the Genotyping and GenomeViewer modules. Chromosomal aberrations were identified by examination of Log R ratios and B-allele frequencies.

MGMT Promoter Methylation Status

The methylation status of the MGMT gene was determined by pyrosequencing as recently described (50). In brief, 0.5 µg genomic DNA was treated with sodium bisulfite using the EpiTect Bisulfite kit (Qiagen, Hilden, Germany) according to the manufacturers recommendations. For pyrosequencing, a 265 bp region was amplified from bisulfite modified genomic DNA using primers MGMT-Py forward, 5'-biotin-GGATATGTTGGGATAGTT-3' (SEQ ID NO: 11) (GenBank accession number AL355531, nucleotides 46891 to 46908) and MGMT-Bis reverse, 5'-AAACTAAACAACACCTAAA-3' (SEQ ID NO: 12) (GenBank accession number AL355531, nucleotides 47138 to 47156) with biotin attached to the 5'-end of the forward primer. The primer used for the extension reaction was 5'-CCCAAACACTCACCAAA-3' (SEQ ID NO: 13) which allowed sequencing of a 63 bp fragment containing 12 CpG sites. The pyrosequencing assay was designed to target CpG sites with strong methylation in GBM. Pyrosequencing was performed using PyroGold Reagents (Qiagen, Hilden, Germany) on the Pyromark Q24 instrument (Biotage, Uppsala, Sweden), according to the manufacturer's instructions. Pyrogram outputs were analyzed by the PyroMark Q24 software (Biotage, Uppsala, Sweden), using the CpG quantification software to determine the percentage of methylated versus unmethylated alleles according to percentage relative peak height. Tumor samples were scored methylated or unmethylated after measuring CpG methylation at individual positions and comparing with methylation data obtained from age matched normal brain tissues. Human reference DNA in vitro methylated by SssI methylase was used as positive control for methylation.

Tumor Xenograft Experiments

Cells were harvested, counted and re-suspended in 0.1% DNase/PBS. Cell vitality was confirmed via trypan blue exclusion. For case #046, $10^6$ DMSO-control (n=5)- or niclosamide (n=5)-pretreated pGBMs were injected stereotactically into the striatum of 12-week old Rag2Il2rg$^{-/-}$ mice (0.8 mm anterior, 2 mm lateral, 3 mm deep). For case #GNV019, 2.5×$10^4$ sham control (Killer Plates® compound 2F05; n=9)- or niclosamide (n=6)-pretreated pGBMs were injected intracranially into P2 to P3 old Scid Beige mice.

Mice were monitored daily and euthanized upon presentation with signs of distress/neurological symptoms or significant weight loss. The #019GNV experiment was terminated at day 169 with one remaining animal that did not appear distressed. For subsequent histological analysis, brains were removed, cryoprotected, and serially cut on a cryostat (Leica) at 20 µm thickness. Every fifth section underwent routine H&E staining for histological analysis of tumor formation.

Statistical Analysis

GraphPad Prism 4.0 software was used for statistical analysis. Data presented with error bars represent mean±SD from triplicate experiments unless otherwise noted. For pharmacodynamic analysis, p-values were calculated using the 1-way ANOVA and Tukey's post-hoc tests (FIG. 1). For multiple comparisons, p-values were calculated using the 1-way ANOVA with Bonferroni post-hoc test. If applicable, the two-sided Student's t test was used to determine statistical significance. A p-value of <0.05 was considered significant.

Results

Niclosamide is a Previously Unrecognized Candidate for GBM Therapy.

A library comprising of 160 synthetic and natural toxic substances was used for the screening approach. Four pGBMs, previously shown to maintain patient- and GBM-specific signatures and to contain sub-populations of tumor cells with and without stem cell qualities served as a discovery platform (#'s 023, 035, 046, 106; see (10)). Primary screening was conducted based on the alamarBlue® assay determining the metabolic activity as a measure for cellular viability at day 5 following single application of the library's compounds. In the experiments, every compound that reduced the mean metabolic activity of the 4 pGBMs below 50% of control levels was considered as a 'hit'. 31 compounds fulfilled this criterion, amongst them niclosamide. Moreover, niclosamide indicated a sufficient potential to address inter-patient heterogeneity by impacting effectively on all four of the tested pGBMs (Table 1) and it demonstrated a cancer-specific potential, as it did not appear to similarly affect hnNCs sample #155, a control case of non-malignant primary adult human neural progenitor cells (AHNPs; (11), Table 1). Niclosamide, revealed a selective pGBM-anticancer potential that had not yet been suggested for treating brain tumors. Niclosamide is known for decades and approved by many regulatory agencies as antihelminthic. Recent work in extra-neural, e.g. preclinical colorectal cancer models suggested some activity of this drug (12, 13). However, given the scarcity of effective cytostatic compounds for the treatment of glioblastoma, its efficacy in this tumor entity was surprising.

TABLE 1

Metabolic activity of different cell lines after application of 1 mM niclosamide for 5 days (results of triplicate analysis), the metabolic inhibition the cells is indicated in % of the activity of a control without niclosamide

| pGBMs[1] | | | | pGBMs average | Controls | |
|---|---|---|---|---|---|---|
| 023 | 035 | 046 | 106 | | 155[2] | U87[3] |
| 32.3 | 5.6 | 34.6 | 33.0 | 26.4 | 75.4 | 66.5 |

[1]primary glioblastoma cell lines used in this study
[2]non-malignant primary adult human neural progenitor cells
[3]a commonly investigated glioma cell line Niclosamide is Effectively and Selectively Inhibiting pGBMs Cellular Viability.

To validate the results obtained from primary screening of the library, pharmacodynamic analysis was conducted using a formulation of niclosamide obtained from Sigma-Aldrich. A total of 21 pGBMs were investigated, including the four cases already used in the screening experiments. The obtained dose-response curves showed consistent courses for all samples (FIG. 1A). The concentrations at which niclosamide induced a 50% reduction of the relative metabolic activity (IC50) ranged from 300 nM to 1.2 µM. This contrasted to the more resistant performance observed in reference- and control-cell samples. The IC50 values of five commonly investigated glioma/GBM cell lines (LN229, T98G, U87, U138, and U373, see methods), here used as a reference, were calculated at 2.4 to 4.2-fold higher concentrations (FIG. 1B; FIG. 6). The lower sensitivity of glioma/GBM cell lines to niclosamide exposure may be due to their standard conditions of maintenance (i.e. serum-containing, mitogen-free), a major factor that in the past might have interfered with many results of drug screening at early developmental stages (7). Further experiments revealed that this assumption is correct. When 'standard GBM model' cell lines (i.e. LN229, T98G, U87(MG), U138, U373(MG)) are maintained under 'dm conditions', i.e. the culture conditions used for maintenance of pGBMs, ND effects are highly similar to findings obtained from pGBMs.

Notably, however, analysis of the three non-malignant hnNCs that were maintained in similar defined culture conditions as pGBMs also revealed a significantly lower level of sensitivity (see methods; FIG. 1B; FIG. 6). This suggested a pGBM-specific activity of niclosamide. When pGBMs and non-malignant hnNCs are co-cultured under dm conditions, the lower sensitivity of hnNCs can be confirmed. These data suggest low levels of ND toxicity on non-malignant neural cells and selective activity against pGBMs.

Considering the cellular and genetic diversity that characterizes GBM, we next investigated niclosamide's pharmacological effect in pGBMs representing key clinical constellations (10, 14-16). Comparative experiments were therefore conducted with samples derived from (i) the tumor core (center) vs. periphery region of the same GBM patient, (ii) primary vs. recurrent disease of the same GBM patient, (iii) MGMT-promoter hypermethylated vs. unmethylated tissue as well as from (iv) GBMs with heterozygous deleted NFKBIA vs. undeleted NFKBIA genotypes (see below). The strong inhibitory activity of niclosamide could be demonstrated similarly in all of these pGBM samples (inset FIG. 1B; FIG. 6). Together, these data confirmed and validated our primary screening results, portraying niclosamide as a highly effective and selective inhibitor of pGBMs.

Niclosamide has Cytostatic, Cytotoxic, and Anti-Migratory Effects in pGBMs.

To further classify the inhibitory activity of niclosamide in pGBMs, studies on cell cycle, vitality, and migratory function were conducted subsequent to a single exposure to the compound. Propidium iodide (PI)-based flow cytometry analysis at revealed a transient G1 phase arrest of pGBMs peaking at 24 to 48 hours (FIG. 2A; FIG. 7). This coincided with a strong decrease of Cyclin D1 expression, a regulator of cell cycle transition from G1 to S phase (FIG. 2B). Evidence for an immediate and transient cytostatic activity was similarly revealed upon examination of pGBM's growth kinetics (FIG. 2C). With a resulting growth delay of 5 days, an additional cytotoxic response became apparent. At this time, pro-apoptotic effects of niclosamide caused a strong and pGBM-selective decrease of vital cells—as observed by phase contrast microscopy (not shown) and as quantified by Hoechst/Annexin V flow cytometric analysis (FIG. 2D). Intriguingly, application of niclosamide at sub-toxic concentrations additionally caused anti-migratory effects on pGBMs, similar to recent findings described for colon cancer cells (12) (FIG. 2E). Thus, niclosamide induced combined cytotoxic, cytostatic, and antimigratory effects in pGBMs.

Niclosamide Inhibits pGBMs Tumor-Initiating Activity.

In a next series of experiments it was aimed to determine the influence of niclosamide on the activity of tumor-initiating cells (TICs). TICs embody a severe functional consequence of intra-tumor heterogeneity as, at least in human GBM, it is anticipated that they are represented by a small subpopulation of stem-like, i.e. self-renewing and multipotent cells (e.g. (17-19)). However, their precise phenotypic characteristics remain elusive (20). We thus applied a combination of assays to measure their responses to niclosamide indirectly. First, the neurosphere assay (NSA) was used to estimate potential alterations to the pool of self-renewing and multipotent cells. In previous studies, we established their frequencies in the range from 0.25 to 1% among culture passage 5-10 pGBMs (see (10)). In the present study, three of these heterogeneous pGBM samples (#'s 046, 078, 106) were exposed to niclosamide, and vital cells were collected at day 5 for processing in the NSA (see methods). Quantification of primary, secondary and tertiary spheres from DMSO-vs. niclosamide pre-treated cells indicated that a single application of niclosamide reduced the frequencies of self-renewing, multipotent cells among pGBMs strongly (FIG. 3A). Because niclosamide did not abolish the multipotent potential among the remaining self-renewing pGBMs at the applied concentration of 1.5 µM (FIG. 3A, inset), it was tempting to speculate that this setting could be used to similarly demonstrate a measurable reduction of tumorigenic cell frequencies in vivo. Parallel long-term growth analysis (CellaVista®, cell confluence-based, see methods) of pGBMs indicated that at this concentration, the recovery of vital cells from cytostatic niclosamide effects had to be expected with a delay of 14-23 days (FIG. 3B). Orthotopic xenotransplantation studies demonstrated, however, that animals engrafted with niclosamide pre-treated vital cells survived considerably longer than expected (FIG. 3C; FIG. 8). The statistic significance of these results was paired with a lower extent to which tumor formation was observed in niclosamide pre-treated cell grafts. In one transplantational series (#GNV019), a single exposure to niclosamide completely extinguished the tumor forming capacity of pGBMs (FIG. 8). In a second experimental series (#046), a strong reduction could be observed. Here, DMSO pre-treated #046 pGBMs that were grafted unilaterally into the striatum elicited severe signs of distress in recipient animals after 88±5d (n=5). Subsequent histological analysis revealed in every of these cases massive intracerebral tumor formation and a strong invasive capacity of engrafted cells along white matter tracts into the contra-lateral hemisphere. By contrast, the tumors that developed in 4/5 animals from niclosamide pre-treated #046 pGBMs at 153±23d after engraftment were smaller of size, with cells accumulating in areas adjacent to the striatal transplant site. Proliferative pGBMs were found clustered in the subventricular zone and dispersed throughout the corpus callosum (FIG. 3E, inset), with individual cells reaching the contra-lateral hemisphere. This corresponded to early post-transplantational stages of DMSO pre-treated #046 cells. Apparently, the diffusely invasive nature of pGBMs sufficed during the long-term experiments to induce neurological dysfunction/distress in the animals that required their euthanization even before the manifestation of an expanding tumor mass. The combined data of our experiments, regardless, suggested strongly that already a single exposure of niclosamide did lead to an effective reduction of tumor initiating activity in pGBMs.

Niclosamide Interferes with Cancer-Driving Signaling Cascades.

It is known that a circumscribed number of transcription factors and associated signaling pathways are overactive in human cancer cells (21). Evidence from previous studies had already suggested that niclosamide interfered with several of these in blood, breast, and colon cancer cells, specifically with Notch-, mTOR-, Wnt-/β-catenin-, and NF-κB-signaling (12, 13, 22-24). Hence, the study focused on this array of pathways for mode of action analysis in pGBMs. Cells were investigated at day 5 after a single-dose exposure to niclosamide (n=4 cases: #'s 046, 078, 81, 106). Western blots demonstrated a concentration-dependent inhibition of Notch pathway activity in the pGBMs, as indicated by decreasing levels of the cleaved Notch 1-protein (FIGS. 4A, 12A and 12C). Similarly, levels of the phosphorylated S6-protein as a major indicator of active mTOR signaling (25) could be shown to decrease in all samples (FIGS. 4B, 12B and 12D). This effect is independent of the NFKBIA gene status. The pleiotropic activity also explains the strong antitumor potential of ND in pre-exposed pGBMs upon orthotopic engraftment in animal models of disease (FIG. 13). Exploration of the Wnt-/β-catenin pathway furthermore suggested a specific interference of niclosamide with the non-canonical (alternative) Akt-dependent regulation of β-catenin's transcriptional activity. Characteristic for the active state of this mechanism, known to play an important role for tumor invasion, is an enhanced nuclear accumulation of β-catenin, phosphorylated at $Ser^{552}$ (26). The respective immunocytochemical exposure and quantification in pGBMs demonstrated a strong decrease of the nuclear phospho-β-catenin (Ser552) antigen in response to application of niclosamide. Consequently, the expression of characteristic β-catenin target genes appeared significantly decreased in the pGBMs (12, 27, 28). Thus, niclosamide revealed a pleiotropic mode of action in pGBMs, inhibiting major cancer-driving signaling cascades simultaneously.

NFKBIA Predicts Synergistic Effects of Niclosamide and Temozolomide.

In contrast to the consistent inhibitory impact on the Notch-, mTOR-, and Wnt-/β-catenin-mediated pathways, niclosamide exhibited a variable effect on NF-κB-signaling in pGBMs. Among the four cases used for mode of action analysis, Western blots revealed for only two (#046 and #078) a pathway inhibition as indicated by decreased levels of the phospho-p65-NFκB protein (FIG. 5A). Subsequent genomic analysis (see methods) demonstrated for these two cases a heterozygous deletion of the NFKBIA locus (NFKBIA$^{+/-}$) at 14q13 that encodes for a major repressor of intracellular NF-κB-signaling. As recent work had suggested that deletion and low expression of NFKBIA were associated with unfavorable clinical outcome in GBM patients (16), additional NFKBIA$^{+/-}$ and NFKBIA$^{+/+}$ pGBMs and standard GBM models were identified from the cohort for further investigation. These samples (pGBMs: n=3 for each group; GBMs: n=2" for each group) revealed baseline expression levels that coincided with the respective genomic status of NFKBIA (inset FIG. 5B; insets of FIGS. 14A and 15A). However, upon exposure to niclosamide, NFKBIA$^{+/-}$ pGBMs as well as standard GBM models under dm conditions were shown to strongly up-regulate their NFKBIA expression (FIGS. 5B, 14A and 15A). As similar responses were not observed in NFKBIA$^{+/+}$ samples, the variable effects of niclosamide on NF-κB-signaling in pGBMs could be explained by a differential stimulation of NFKBIA expression in the NFKBIA$^{+/-}$ samples. This observation intrigued, as it is known that down-regulation of NFKBIA in GBM cells is associated with a lack of response to alkylating agents, e.g. the standard GBM chemotherapeutic TMZ (29). On the other hand, it is known that the inhibition of NF-κB alone may not severely affect most solid tumors, rather that it may help to prevent resistance of cancer cells to chemotherapy (30, 31). Thus, a potential benefit that a combined application of niclosamide and TMZ might have in this setting was investigated.

TABLE 2

Combinatorial index evaluation for treatment with niclosamide plus TMZ in pGBMs indicates synergistic activity.

| Case # | NFKBIA status | Expected survival proportion | Observed survival proportion | Combinatorial index |
|---|---|---|---|---|
| 046 | +/− | 0.562 | 0.319 | 0.567 |
| 078 | +/− | 0.375 | 0.283 | 0.754 |
| 118 | +/− | 0.806 | 0.392 | 0.486 |
| 138 | +/− | 0.417 | 0.261 | 0.625 |
| 66  | +/+ | 0.705 | 0.720 | 0.979 |
| 81  | +/+ | 0.406 | 0.363 | 0.886 |
| 106 | +/+ | 0.819 | 0.731 | 0.901 |

The combinatorial indices (CIs) for niclosamide and TMZ were expressed as ratio of observed vs. expected cell viability. Expected results were calculated as the proportion of viable cells following treatment with (only) 1 μM niclosamide multiplied by the proportion of cells following treatment with (only) TMZ. (CI<1:synergy, CI=1:additive; CI>1: antagonism). NFKBIA status +/− (heterozygous deletion), +/+ (not deleted).

Experiments employed a cohort of 7 pGBMs (n=4, NFKBIA$^{+/-}$; n=3 NFKBIA$^{+/+}$; Table 2) and four standard GBM cell lines. All of these samples showed an unmethylated MGMT promoter status, a condition that indicates poor clinical responses to standard radio/TMZ-chemotherapy (2, 16). Combinatorial index analysis of niclosamide was conducted in the presence of 50 μM TMZ. Combinatorial indizes of pGBMs and GBMs are given in FIGS. 14B and 15B. The concentration of TMZ was chosen based on the reported plasma peak levels in patients (32), which in many previous studies had shown to impact very little on the viability of glioma cells maintained in vitro (10, 33, 34). Similarly, we here observed that application of 50 μM TMZ to the pGBMs reduced their metabolic activity of pGBMs to only 94±4% of control levels (n=7, triplicate analysis; data not shown) and the activity of GBMs to only 89±8%. In combination with niclosamide, however, TMZ showed a particular effect on NFKBIA$^{+/-}$ pGBM as well as GBM samples. Their dose-response curves showed a remarkable left-shift indicating stronger inhibitory activity of combined niclosamide/TMZ application compared to the NFKBIA$^{+/+}$ samples (FIGS. 5C, 14C and 15C). Calculation of the combinatorial index (CI; (35)) suggested for NFKBIA$^{+/+}$ pGBMs approximately additive effects (CI=0.92±0.05), and a clear synergistic activity of niclosamide/TMZ in all NFKBIA$^{+/-}$ samples (CI=0.61±0.11) (Table 1).

Similar results were obtained for standard cell lines (see FIG. 15).

To directly demonstrate the involvement of NFκB in the observed synergistic activity, we performed control studies using the NFκB activator TNFα (Peprotech). Application of TNFα activated NFκB in pGBMs, and in accordance to our hypothesis, counteracted synergy effects in NFKBIA+/− genotypes (FIG. 16).

These data suggested that niclosamide augments the anticancer effects of TMZ, the current GBM standard chemotherapeutic. Based on determining the genomic status of NFKBIA in GBM cells, a synergistic effect of niclosamide and TMZ may furthermore become predictable.

Discussion

The combined data of this study indicate that the pleiotropic anticancer effects of niclosamide are ideally suited to inhibit pGBMs from a variety of key clinical constellations. Cytostatic, cytotoxic, and anti-migratory effects are elicited, and the stem-like/tumorigenic cell fraction among pGBMs is strongly reduced. Thus, the issues of inter- and intra-patient tumor heterogeneity as well as the invasive nature of glial tumor cells that complicate any therapeutic approach in GBM (36) may become accessible by one drug. Several unique features of this compound nevertheless warrant future investigation for translation to brain tumor therapy. Niclosamide is a common, by many regulatory agencies approved antihelminthic that has not yet been considered for the treatment of brain tumors. It is a salicylanilide, a chemical derivative of salicylic acid that was introduced by Bayer as a molluscide in 1959. For medical use in animals and humans oral application is preferred causing only little toxicity. Studies in animals suggested no mutagenic, oncogenic, or embryotoxic activity and no cumulative effects. Its rate of absorption from the intestinal tract was estimated at 33% (for cumulative review, see (37)). The in vitro data suggest that niclosamide inhibits GBM core and periphery cells from primary disease, from disease recurrence, from MGMT promoter methylated and unmethylated, as well as from NFKBIA$^{+/+}$ and NFKBIA$^{+/-}$ GBM samples in concentration ranges that only marginally affect human non-malignant neural (control) cells.

For mode of action analysis, this study hays mostly relied on evidence from previous work in the fields of hemato-oncology, colon, and breast cancer research (12, 13, 22-24). The findings of the present study have confirmed the results of these studies, exposing pleitropic inhibitory effects of niclosamide on Wnt-/β-catenin-, Notch-, and mTor-signaling, which are known to play a pivotal role for GBM malignancy as well (16, 38-40). Of particular interest for future clinical application is niclosamide's hitherto unrecognized attribute to stimulate NFKBIA expression in NFKBIA$^{+/-}$ cancer genotypes. While the responsible mechanism remains yet unclear, the resulting inhibition of NF-κB activity could be used to overcome resistance to alkylating agents such as TMZ (29). The here demonstrated synergistic activity of niclosamide with the current standard GBM chemotherapeutic TMZ in NFKBIA$^{+/-}$ pGBMs provides evidence for this assumption. It is highly probable that other cancer entities presenting with specific single-nucleotide polymorphisms and haplotypes of NFKBIA, e.g. Hodgkin's lymphoma, colorectal cancer, melanoma, hepatocellular carcinoma, breast cancer, and multiple myeloma (for collective references, see (16)) might profit from combining niclosamide with alkylating chemotherapeutic regimens.

REFERENCES

1. Chabner, B. A., and Roberts, T. G., Jr. 2005. Timeline: Chemotherapy and the war on cancer. Nat Rev Cancer 5:65-72.
2. Hegi, M. E., Diserens, A. C., Gorlia, T., Hamou, M. F., de Tribolet, N., Weller, M., Kros, J. M., Hainfellner, J. A., Mason, W., Mariani, L., et al. 2005. MGMT gene silencing and benefit from temozolomide in glioblastoma. N Engl J Med 352:997-1003.
3. Stupp, R., Hegi, M. E., Mason, W. P., van den Bent, M. J., Taphoorn, M. J., Janzer, R. C., Ludwin, S. K., Allgeier, A., Fisher, B., Belanger, K., et al. 2009. Effects of radiotherapy with concomitant and adjuvant temozolomide versus radiotherapy alone on survival in glioblastoma in a randomised phase III study: 5-year analysis of the EORTC-NCIC trial. Lancet Oncol 10:459-466.
4. Swinney, D. C., and Anthony, J. 2011. How were new medicines discovered? Nat Rev Drug Discov 10:507-519.
5. Kola, I., and Landis, J. 2004. Can the pharmaceutical industry reduce attrition rates? Nat Rev Drug Discov 3:711-715.
6. Damia, G., and D'Incalci, M. 2009. Contemporary preclinical development of anticancer agents—what are the optimal preclinical models? Eur J Cancer 45:2768-2781.
7. Sharma, S. V., Haber, D. A., and Settleman, J. 2010. Cell line-based platforms to evaluate the therapeutic efficacy of candidate anticancer agents. Nat Rev Cancer 10:241-253.
8. Lee, J., Kotliarova, S., Kotliarov, Y., Li, A., Su, Q., Donin, N. M., Pastorino, S., Purow, B. W., Christopher, N., Zhang, W., et al. 2006. Tumor stem cells derived from glioblastomas cultured in bFGF and EGF more closely mirror the phenotype and genotype of primary tumors than do serum-cultured cell lines. Cancer Cell 9:391-403.
9. Pollard, S. M., Yoshikawa, K., Clarke, I. D., Danovi, D., Stricker, S., Russell, R., Bayani, J., Head, R., Lee, M., Bernstein, M., et al. 2009. Glioma stem cell lines expanded in adherent culture have tumor-specific phenotypes and are suitable for chemical and genetic screens. Cell Stem Cell 4:568-580.
10. Glas, M., Rath, B. H., Simon, M., Reinartz, R., Schramme, A., Trageser, D., Eisenreich, R., Leinhaas, A., Keller, M., Schildhaus, H. U., et al. 2010. Residual tumor cells are unique cellular targets in glioblastoma. Ann Neurol 68:264-269.
11. Walton, N. M., Sutter, B. M., Chen, H. X., Chang, L. J., Roper, S. N., Scheffler, B., and Steindler, D. A. 2006. Derivation and large-scale expansion of multipotent astroglial neural progenitors from adult human brain. Development 133:3671-3681.
12. Sack, U., Walther, W., Scudiero, D., Selby, M., Kobelt, D., Lemm, M., Fichtner, I., Schlag, P. M., Shoemaker, R. H., and Stein, U. 2011. Novel effect of antihelminthic Niclosamide on S100A4-mediated metastatic progression in colon cancer. J Natl Cancer Inst 103:1018-1036.
13. Osada, T., Chen, M., Yang, X. Y., Spasojevic, I., Vandeusen, J. B., Hsu, D., Clary, B. M., Clay, T. M., Chen, W., Morse, M. A., et al. 2011. Antihelminth compound niclosamide downregulates Wnt signaling and elicits antitumor responses in tumors with activating APC mutations. Cancer Res 71:4172-4182.
14. Simpson, L., and Galanis, E. 2006. Recurrent glioblastoma multiforme: advances in treatment and promising drug candidates. Expert Rev Anticancer Ther 6:1593-1607.
15. Weller, M., Stupp, R., Reifenberger, G., Brandes, A. A., van den Bent, M. J., Wick, W., and Hegi, M. E. 2010. MGMT promoter methylation in malignant gliomas: ready for personalized medicine? Nat Rev Neurol 6:39-51.
16. Bredel, M., Scholtens, D. M., Yadav, A. K., Alvarez, A. A., Renfrow, J. J., Chandler, J. P., Yu, I. L., Carro, M. S., Dai, F., Tagge, M. J., et al. 2011. NFKBIA deletion in glioblastomas. N Engl J Med 364:627-637.
17. Stiles, C. D., and Rowitch, D. H. 2008. Glioma stem cells: a midterm exam. Neuron 58:832-846.
18. Zhou, B. B., Zhang, H., Damelin, M., Geles, K. G., Grindley, J. C., and Dirks, P. B. 2009. Tumour-initiating cells: challenges and opportunities for anticancer drug discovery. Nat Rev Drug Discov 8:806-823.
19. Nguyen, L. V., Vanner, R., Dirks, P., and Eaves, C. J. 2012. Cancer stem cells: an evolving concept. Nat Rev Cancer 12:133-143.
20. Westphal, M., and Lamszus, K. 2011. The neurobiology of gliomas: from cell biology to the development of therapeutic approaches. Nat Rev Neurosci 12:495-508.
21. Darnell, J. E., Jr. 2002. Transcription factors as targets for cancer therapy. Nat Rev Cancer 2:740-749.
22. Balgi, A. D., Fonseca, B. D., Donohue, E., Tsang, T. C., Lajoie, P., Proud, C. G., Nabi, I. R., and Roberge, M. 2009. Screen for chemical modulators of autophagy reveals novel therapeutic inhibitors of mTORC1 signaling. PLoS One 4:e7124.
23. Wang, A. M., Ku, H. H., Liang, Y. C., Chen, Y. C., Hwu, Y. M., and Yeh, T. S. 2009. The autonomous notch signal pathway is activated by baicalin and baicalein but is suppressed by niclosamide in K562 cells. J Cell Biochem 106:682-692.
24. Jin, Y., Lu, Z., Ding, K., Li, J., Du, X., Chen, C., Sun, X., Wu, Y., Zhou, J., and Pan, J. 2010. Antineoplastic mechanisms of niclosamide in acute myelogenous leukemia stem cells: inactivation of the NF-kappaB pathway and generation of reactive oxygen species. Cancer Res 70:2516-2527.
25. Wullschleger, S., Loewith, R., and Hall, M. N. 2006. TOR signaling in growth and metabolism. Cell 124:471-484.
26. Fang, D., Hawke, D., Zheng, Y., Xia, Y., Meisenhelder, J., Nika, H., Mills, G. B., Kobayashi, R., Hunter, T., and Lu, Z. 2007. Phosphorylation of beta-catenin by AKT promotes beta-catenin transcriptional activity. J Biol Chem 282:11221-11229.
27. Clevers, H. 2006. Wnt/beta-catenin signaling in development and disease. Cell 127:469-480.
28. Moon, R. T., Kohn, A. D., De Ferrari, G. V., and Kaykas, A. 2004. WNT and beta-catenin signalling: diseases and therapies. Nat Rev Genet 5:691-701.
29. Bredel, M., Bredel, C., Juric, D., Duran, G. E., Yu, R. X., Harsh, G. R., Vogel, H., Recht, L. D., Scheck, A. C., and Sikic, B. I. 2006. Tumor necrosis factor-alpha-induced protein 3 as a putative regulator of nuclear factor-kappaB-mediated resistance to alkylating agents in human glioblastomas. J Clin Oncol 24:274-287.
30. Baldwin, A. S. 2001. Control of oncogenesis and cancer therapy resistance by the transcription factor NF-kappaB. J Clin Invest 107:241-246.
31. Nakanishi, C., and Toi, M. 2005. Nuclear factor-kappaB inhibitors as sensitizers to anticancer drugs. Nat Rev Cancer 5:297-309.
32. Brada, M., Judson, I., Beale, P., Moore, S., Reidenberg, P., Statkevich, P., Dugan, M., Batra, V., and Cutler, D. 1999. Phase I dose-escalation and pharmacokinetic study 33. Hermisson, M., Klumpp, A., Wick, W., Wischhusen, J., Nagel, G., Roos, W., Kaina, B., and Weller, M. 2006. $O^6$-methylguanine DNA methyltransferase and p53 status predict temozolomide sensitivity in human malignant glioma cells. J Neurochem 96:766-776.
34. Beier, D., Rohrl, S., Pillai, D. R., Schwarz, S., Kunz-Schughart, L. A., Leukel, P., Proescholdt, M., Brawanski, A., Bogdahn, U., Trampe-Kieslich, A., et al. 2008. Temozolomide preferentially depletes cancer stem cells in glioblastoma. Cancer Res 68:5706-5715.
35. Chou, T. C. 2010. Drug combination studies and their synergy quantification using the Chou-Talalay method. Cancer Res 70:440-446.
36. Bonavia, R., Inda, M. M., Cavenee, W. K., and Furnari, F. B. 2011. Heterogeneity maintenance in glioblastoma: a social network. Cancer Res 71:4055-4060.
37. Andrews, P., Thyssen, J., and Lorke, D. 1982. The biology and toxicology of molluscicides, Bayluscide. Pharmacol Ther 19:245-295.
38. Zhang, N., Wei, P., Gong, A., Chiu, W. T., Lee, H. T., Colman, H., Huang, H., Xue, J., Liu, M., Wang, Y., et al. 2011. FoxMl promotes beta-catenin nuclear localization and controls Wnt target-gene expression and glioma tumorigenesis. Cancer Cell 20:427-442.
39. Zhu, T. S., Costello, M. A., Talsma, C. E., Flack, C. G., Crowley, J. G., Hamm, L. L., He, X., Hervey-Jumper, S. L., Heth, J. A., Muraszko, K. M., et al. 2011. Endothelial cells create a stem cell niche in glioblastoma by providing NOTCH ligands that nurture self-renewal of cancer stem-like cells. Cancer Res 71:6061-6072.
40. Akhavan, D., Cloughesy, T. F., and Mischel, P. S. 2010. mTOR signaling in glioblastoma: lessons learned from bench to bedside. Neuro Oncol 12:882-889.
41. Barretina, J., Caponigro, G, Stransky, N., Venkatesan, K., Margolin, A. A., Kim, S., Wilson, C. J., Lehar, J., Kryukov, G. V., Sonkin, D., et al. 2012. The Cancer Cell Line Encyclopedia enables predictive modelling of anticancer drug sensitivity. Nature 483:603-607.
42. Cao, X., Shores, E. W., Hu-Li, J., Anver, M. R., Kelsall, B. L., Russell, S. M., Drago, J., Noguchi, M., Grinberg, A., Bloom, E. T., et al. 1995. Defective lymphoid development in mice lacking expression of the common cytokine receptor gamma chain. Immunity 2:223-238.
43. Louis, D. N., Ohgaki, H., Wiestler, O. D., Cavenee, W. K., Burger, P. C., Jouvet, A., Scheithauer, B. W., and Kleihues, P. 2007. The 2007 WHO classification of tumours of the central nervous system. Acta Neuropathol 114:97-109.
44. Scheffler, B., Walton, N. M., Lin, D. D., Goetz, A. K., Enikolopov, G., Roper, S. N., and Steindler, D. A. 2005. Phenotypic and functional characterization of adult brain neuropoiesis. Proc Natl Acad Sci USA 102:9353-9358.
45. Koch, P., Opitz, T., Steinbeck, J. A., Ladewig, J., and Brustle, O. 2009. A rosette-type, self-renewing human ES cell-derived neural stem cell with potential for in vitro instruction and synaptic integration. Proc Natl Acad Sci USA 106:3225-3230.
46. Falk, A., Koch, P., Kesavan, J., Takashima, Y., Ladewig, J., Alexander, M., Wiskow, O., Tailor, J., Trotter, M., Pollard, S., et al. 2012. Capture of neuroepithelial-like stem cells from pluripotent stem cells provides a versatile system for in vitro production of human neurons. PLoS One 7:e29597.
47. Koch, P., Breuer, P., Peitz, M., Jungverdorben, J., Kesavan, J., Poppe, D., Doerr, J., Ladewig, J., Mertens, J., Tuting, T., et al. 2011. Excitation-induced ataxin-3 aggregation in neurons from patients with Machado-Joseph disease. Nature.
48. Goetz, A. K., Scheffler, B., Chen, H. X., Wang, S., Suslov, O., Xiang, H., Brustle, O., Roper, S. N., and Steindler, D. A. 2006. Temporally restricted substrate interactions direct fate and specification of neural precursors derived from embryonic stem cells. Proc Natl Acad Sci USA 103:11063-11068.
49. Wiechen, K., Diatchenko, L., Agoulnik, A., Scharff, K. M., Schober, H., Arlt, K., Zhumabayeva, B., Siebert, P. D., Dietel, M., Schafer, R., et al. 2001. Caveolin-1 is down-regulated in human ovarian carcinoma and acts as a candidate tumor suppressor gene. Am J Pathol 159:1635-1643.
50. Mikeska, T., Bock, C., El-Maarri, O., Hubner, A., Ehrentraut, D., Schramm, J., Felsberg, J., Kahl, P., Buttner, R., Pietsch, T., et al. 2007. Optimization of quantitative MGMT promoter methylation analysis using pyrosequencing and combined bisulfite restriction analysis. J Mol Diagn 9:368-381.

The invention claimed is:

1. A method of treating a solid tumor, comprising administering a cytostatic compound according to formula I, II or III

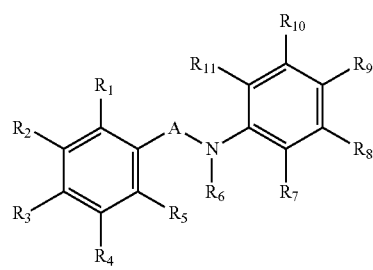

(I)

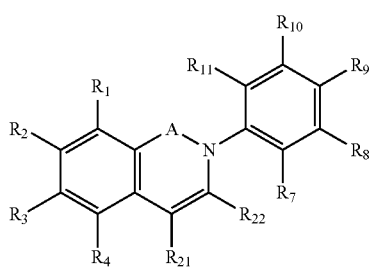

(II)

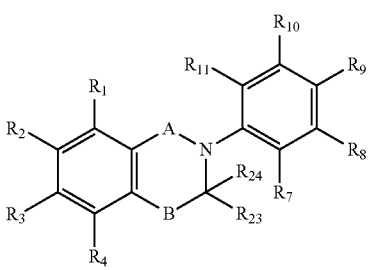

(III)

wherein

A is carbonyl, methylene, hydroxymethinyl, alkoxymethinyl, aminomethinyl, oxime, hydrazone, arylhydrazone, or semicarbazone;

B if present is $CR_{25}R_{26}$, O, S or $NR_{27}$;

$R_1$, $R_3$, $R_4$, $R_8$, $R_{10}$, and $R_{11}$ are independently hydrogen, hydroxyl, alkoxy, halogen or $C_1$ to $C_6$ alkyl;

$R_2$ and $R_7$ are independently halogen, hydroxyl or hydrogen, $R_5$ if present is hydroxyl, phosphate, hydrogen, halogen, alkyl, cycloalykyl, alkenyl, alkynyl, aryl, alkoxy, alkylthio or amino;

$R_6$ if present is hydrogen or $C_1$ to $C_6$ alkyl;

$R_9$ is nitro, hydrogen, hydroxyl, amino, halogen, alkyl, alkenyl, alkynyl, or aryl; and $R_{21}$, $R_{22}$, $R_{23}$, and $R_{24}$, if present are independently hydrogen, hydroxyl, halogen, alkyl, alkenyl, alkynyl, cycloalkyl or aryl;

$R_{25}$ and $R_{26}$ if present are independently hydrogen, hydroxyl, halogen, alkyl, alkenyl, alkynyl, cycloalkyl or aryl; and $R_{27}$ if present is hydrogen or $C_1$ to $C_6$ alkyl;

or salt thereof;

and an alkylating agent to a subject.

2. The method of claim 1, wherein the alkylating agent is an $O^6$-alkylating agent.

3. The method of claim 1, wherein the alkylating agent has a structure according to formula IV

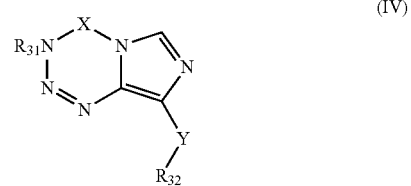

(IV)

wherein
X and Y are independently carbonyl, methylene, hydroxymethinyl, alkoxymethinyl, aminomethinyl, oxime, hydrazone, arylhydrazone or semicarbazone, $R_{31}$ is alkyl, hydrogen, alkoxy, alkenyl, alkynyl, cycloalkyl or aryl; and $R_{32}$ is amino, hydrogen, hydroxyl or halogen or salt thereof.

4. The method of claim 1, wherein the cytostatic compound is niclosamide.

5. The method of claim 1, wherein the alkylating agent is temozolomide.

6. The method of claim 4, wherein the molar ratio between niclosamide and temozolomide is in the range of 10% niclosamide/90% temozolomide to 90% niclosamide/10% temozolomide.

7. The method of claim 1, wherein the solid tumor is glioblastoma.

8. The method of claim 7, wherein the glioblastoma is primary glioblastoma, de novo glioblastoma, secondary glioblastoma, recurrent glioblastoma, glioblastoma with increased methylation of the promoter of the gene O6-Methylguanin-Methyltransferase (MGMT), glioblastoma without increased methylation of the promoter of MGMT, glioblastoma with mutated p53, glioblastoma without mutated p53, glioblastoma with alterations of the gene encoding kappa light polypeptide gene enhancer in B-cells inhibitor (NFκBIA), glioblastoma without alterations of the gene encoding NFκBIA, glioblastoma with alterations of the gene encoding epidermal growth factor receptor (EGFR), glioblastoma without alterations of the gene encoding EGFR, glioblastoma with alterations of the gene encoding platelet-derived growth factor receptor (PDGFRA), glioblastoma without alterations of the gene encoding PDGFRA, glioblastoma with alterations of the gene encoding isocitrate dehydrogenase 1 (IDHI), glioblastoma without alterations of the gene encoding IDHI, glioblastoma with alterations of the gene encoding neurofibromatosis type 1 (NF1) or glioblastoma without alterations of the gene encoding NF1.

9. The method of claim 1, wherein the compounds are formulated for simultaneous or subsequent administration.

10. The method of claim 9, wherein the formulation for simultaneous administration is a mixture of the two compounds.

11. The method of claim 1, wherein the cytostatic compound is formulated for resorption into the central nervous system.

12. A pharmaceutical composition comprising a cytostatic compound according to formula I, II or III

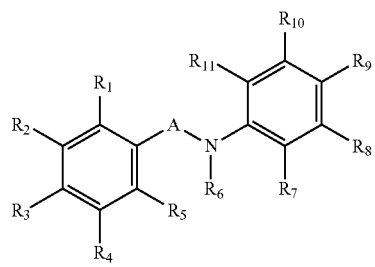

(I)

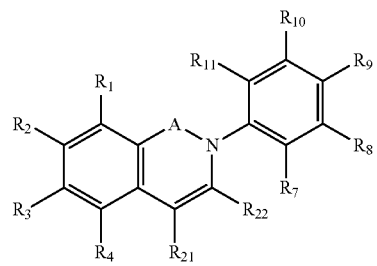

(II)

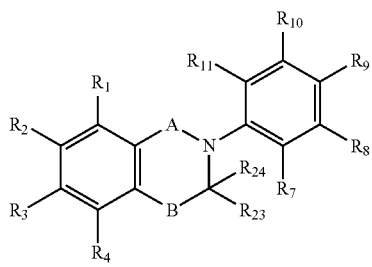

(III)

wherein

A is carbonyl, methylene, hydroxymethinyl, alkoxymethinyl, aminomethinyl, oxime, hydrazone, arylhydrazone, or semicarbazone;

B if present is $CR_{25}R_{26}$, O, S or $NR_{27}$;

$R_1$, $R_3$, $R_4$, $R_8$, $R_{10}$, and $R_{11}$ are independently hydrogen, hydroxyl, alkoxy, halogen or $C_1$ to $C_6$ alkyl;

$R_2$ and $R_7$ are independently halogen, hydroxyl or hydrogen, $R_5$ if present is hydroxyl, phosphate, hydrogen, halogen, alkyl, cycloalykyl, alkenyl, alkynyl, aryl, alkoxy, alkylthio or amino;

$R_6$ if present is hydrogen or $C_1$ to $C_6$ alkyl;

$R_9$ is nitro, hydrogen, hydroxyl, amino, halogen, alkyl, alkenyl, alkynyl, or aryl; and $R_{21}$, $R_{22}$, $R_{23}$, and $R_{24}$, if present are independently hydrogen, hydroxyl, halogen, alkyl, alkenyl, alkynyl, cycloalkyl or aryl;

$R_{25}$ and $R_{26}$ if present are independently hydrogen, hydroxyl, halogen, alkyl, alkenyl, alkynyl, cycloalkyl or aryl; and $R_{27}$ if present is hydrogen or $C_1$ to $C_6$ alkyl:

or salt thereof;

an alkylating agent;

and a pharmaceutically acceptable excipient.

13. A method of treating a solid tumor characterized by a decreased expression level of NFκBIA, comprising administering a cytostatic compound according to formula I, II or III

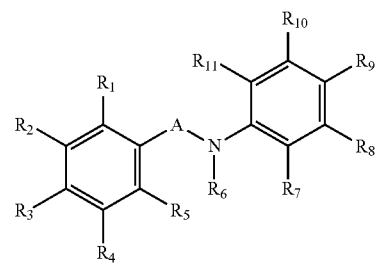

(I)

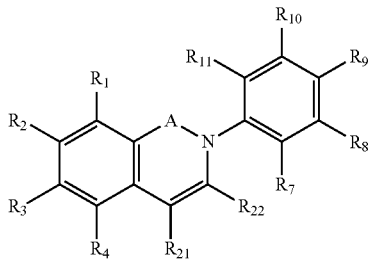
(II)

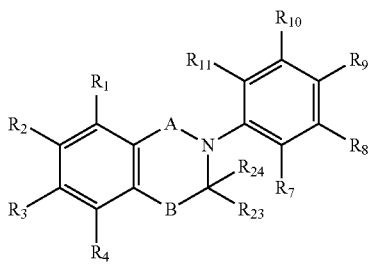
(III)

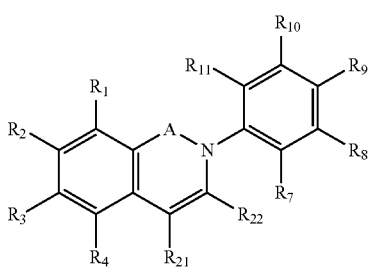
(II)

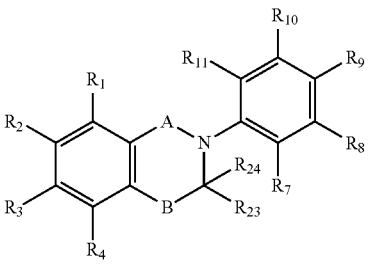
(III)

to a subject, wherein

A is carbonyl, methylene, hydroxymethinyl, alkoxymethinyl, aminomethinyl, oxime, hydrazone, arylhydrazone, or semicarbazone;

B if present is $CR_{25}R_{26}$, O, S or $NR_{27}$;

$R_1$, $R_3$, $R_4$, $R_8$, $R_{10}$, and $R_{11}$ are independently hydrogen, hydroxyl, alkoxy, halogen or $C_1$ to $C_6$ alkyl;

$R_2$ and $R_7$ are independently halogen, hydroxyl or hydrogen, $R_5$ if present is hydroxyl, phosphate, hydrogen, halogen, alkyl, cycloalykyl, alkenyl, alkynyl, aryl, alkoxy, alkylthio or amino;

$R_6$ if present is hydrogen or $C_1$ to $C_6$ alkyl;

$R_9$ is nitro, hydrogen, hydroxyl, amino, halogen, alkyl, alkenyl, alkynyl, or aryl; and $R_{21}$, $R_{22}$, $R_{23}$, and $R_{24}$, if present are independently hydrogen, hydroxyl, halogen, alkyl, alkenyl, alkynyl, cycloalkyl or aryl;

$R_{25}$ and $R_{26}$ if present are independently hydrogen, hydroxyl, halogen, alkyl, alkenyl, alkynyl, cycloalkyl or aryl; and $R_{27}$ if present is hydrogen or $C_1$ to $C_6$ alkyl.

14. A method for determining if therapy with a cytostatic compound according to formula I, II or III

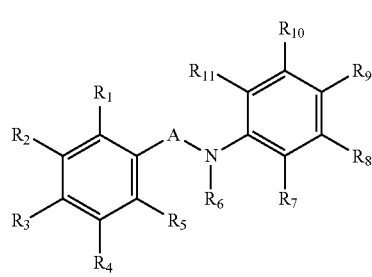
(I)

wherein

A is carbonyl, methylene, hydroxymethinyl, alkoxymethinyl, aminomethinyl, oxime, hydrazone, arylhydrazone, or semicarbazone;

B if present is $CR_{25}R_{26}$, O, S or $NR_{27}$;

$R_1$, $R_3$, $R_4$, $R_8$, $R_{10}$, and $R_{11}$ are independently hydrogen, hydroxyl, alkoxy, halogen or $C_1$ to $C_6$ alkyl;

$R_2$ and $R_7$ are independently halogen, hydroxyl or hydrogen, $R_5$ if present is hydroxyl, phosphate, hydrogen, halogen, alkyl, cycloalykyl, alkenyl, alkynyl, aryl, alkoxy, alkylthio or amino;

$R_6$ if present is hydrogen or $C_1$ to $C_6$ alkyl;

$R_9$ is nitro, hydrogen, hydroxyl, amino, halogen, alkyl, alkenyl, alkynyl, or aryl; and $R_{21}$, $R_{22}$, $R_{23}$, and $R_{24}$, if present are independently hydrogen, hydroxyl, halogen, alkyl, alkenyl, alkynyl, cycloalkyl or aryl;

$R_{25}$ and $R_{26}$ if present are independently hydrogen, hydroxyl, halogen, alkyl, alkenyl, alkynyl, cycloalkyl or aryl; and $R_{27}$ if present is hydrogen or $C_1$ to $C_6$ alkyl, is suitable for treating a patient with a solid tumor comprising the steps of a) determining the expression level of NFκBIA in a sample of tumor cells or tumor tissue of the patient;

b) comparing the determined expression level with a reference value;

c) determining if the therapy with niclosamide is suitable for the patient based on the result of the comparison of step b), wherein underexpression or a deletion of NFκBIA indicates that the combination therapy is suitable for the patient.

15. A method for determining the molar ratio of niclosamide to temozolomide to be administered to a patient with a solid tumor comprising the steps of a) determining the expression level of NFκBIA in a sample of tumor cells or tumor tissue of the patient;

b) comparing the determined expression level with a reference value;

c) determining the molar ratio of niclosamide to temozolomide based on the result of the comparison of step b), wherein (i) an expression above the reference value indicates that the molar ratio shall be below 40% niclosamide; and
(ii) an expression level below the reference value indicates that the molar ratio shall be equal to or larger than 40% niclosamide.

16. The method of claim 13, wherein the solid tumor is glioblastoma.

17. The method of claim 16, wherein the glioblastoma is primary glioblastoma, de novo glioblastoma, secondary glioblastoma, recurrent glioblastoma, glioblastoma with increased methylation of the promoter of the gene O6-Methylguanin-Methyltransferase (MGMT), glioblastoma without increased methylation of the promoter of MGMT, glioblastoma with mutated p53, glioblastoma without mutated p53, glioblastoma with alterations of the gene encoding kappa light polypeptide gene enhancer in B-cells inhibitor (NFκBIA), glioblastoma without alterations of the gene encoding NFκBIA, glioblastoma with alterations of the gene encoding epidermal growth factor receptor (EGFR), glioblastoma without alterations of the gene encoding EGFR, glioblastoma with alterations of the gene encoding platelet-derived growth factor receptor (PDGFRA), glioblastoma without alterations of the gene encoding PDGFRA, glioblastoma with alterations of the gene encoding isocitrate dehydrogenase 1 (IDHI), glioblastoma without alterations of the gene encoding IDHI, glioblastoma with alterations of the gene encoding neurofibromatosis type 1 (NF1) or glioblastoma without alterations of the gene encoding NF1.

* * * * *

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="PCR primer"
      /organism="Artificial Sequence"

<400> SEQUENCE: 1
ctcagcgctt cttctttc                                                  18

<210> SEQ ID NO 2
<211> LENGTH: 18
<212> TYPE: DNA
<213> ORGANISM: Artificial Sequence
```

```
<220> FEATURE:
<221> NAME/KEY: source
<222> LOCATION: 1..18
<223> OTHER INFORMATION: /mol_type="DNA"
      /note="PCR primer"
      /organism="Artificial Sequence"

<400> SEQUENCE: 2
gggtcagcag ctcccttta                                              18

<210> SEQ ID NO 3
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="PCR primer"
      /organism="Artificial Sequence"

<400> SEQUENCE: 3
ttcgggtagt ggaaaaccag                                             20

<210> SEQ ID NO 4
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="PCR primer"
      /organism="Artificial Sequence"

<400> SEQUENCE: 4
cagcagctcg aatttcttcc                                             20

<210> SEQ ID NO 5
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="PCR primer"
      /organism="Artificial Sequence"

<400> SEQUENCE: 5
ccgtccatgc ggaagatc                                               18

<210> SEQ ID NO 6
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="DNA"
      /note="PCR primer"
      /organism="Artificial Sequence"

<400> SEQUENCE: 6
atggccagcg ggaagac                                                17

<210> SEQ ID NO 7
<211> LENGTH: 20
<212> TYPE: DNA
```

```
<213> ORGANISM: Artificial Sequence
<220> FEATURE:
<221> NAME/KEY: source
<222> LOCATION: 1..20
<223> OTHER INFORMATION: /mol_type="DNA"
      /note="PCR primer"
      /organism="Artificial Sequence"

<400> SEQUENCE: 7
acaccaggtc aggattttgc                                                  20

<210> SEQ ID NO 8
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="PCR primer"
      /organism="Artificial Sequence"

<400> SEQUENCE: 8
gctgatgtca atgctcagga                                                  20

<210> SEQ ID NO 9
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="PCR primer"
      /organism="Artificial Sequence"

<400> SEQUENCE: 9
tgcaccacca actgcttagc                                                  20

<210> SEQ ID NO 10
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="DNA"
      /note="PCR primer"
      /organism="Artificial Sequence"

<400> SEQUENCE: 10
ggcatggact gtggtcatga g                                                21

<210> SEQ ID NO 11
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="PCR primer"
      /organism="Artificial Sequence"

<400> SEQUENCE: 11
ggatatgttg ggatagtt                                                    18

<210> SEQ ID NO 12
<211> LENGTH: 19
```

```
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="PCR primer"
      /organism="Artificial Sequence"

<400> SEQUENCE: 12
aaactaaaca acacctaaa                                                19

<210> SEQ ID NO 13
<211> LENGTH: 17
<212> TYPE: DNA
<213> ORGANISM: Artificial Sequence
<220> FEATURE:
<221> NAME/KEY: source
<222> LOCATION: 1..17
<223> OTHER INFORMATION: /mol_type="DNA"
      /note="PCR primer"
      /organism="Artificial Sequence"

<400> SEQUENCE: 13
cccaaacact caccaaa                                                  17
```